US008153426B2

(12) United States Patent
Moser et al.

(10) Patent No.: US 8,153,426 B2
(45) Date of Patent: Apr. 10, 2012

(54) PREPARATION OF ANTIGEN-PRESENTING HUMAN GAMMA-DELTA T CELLS AND USE IN IMMUNOTHERAPY

(75) Inventors: Bernhard Moser, Utzenstorf (CH); Marlene Brandes Kuchen, Bethesda, MD (US)

(73) Assignee: University College Cardiff Consultants Limited, Cardiff (GB)

( * ) Notice: Subject to any disclaimer, the term of this patent is extended or adjusted under 35 U.S.C. 154(b) by 549 days.

(21) Appl. No.: 11/573,912

(22) PCT Filed: Aug. 11, 2005

(86) PCT No.: PCT/CH2005/000469
§ 371 (c)(1),
(2), (4) Date: Jun. 6, 2007

(87) PCT Pub. No.: WO2006/017954
PCT Pub. Date: Feb. 23, 2006

(65) Prior Publication Data
US 2008/0075732 A1    Mar. 27, 2008

(30) Foreign Application Priority Data

Aug. 19, 2004 (EP) .................................. 04405516
Apr. 1, 2005 (EP) .................................. 05007214

(51) Int. Cl.
*C12N 5/071* (2010.01)
*C12N 5/0783* (2010.01)
*C12N 15/00* (2006.01)

(52) U.S. Cl. ...................... 435/374; 435/372.3; 435/455

(58) Field of Classification Search ........................ None
See application file for complete search history.

(56) References Cited

U.S. PATENT DOCUMENTS

| 5,747,332 | A | 5/1998 | Wallen et al. |
| 5,788,963 | A | 8/1998 | Murphy et al. |
| 6,274,378 | B1 | 8/2001 | Steinman et al. |
| 2005/0009008 | A1 | 1/2005 | Robinson et al. |
| 2005/0196385 | A1 | 9/2005 | Romagne et al. |
| 2006/0194755 | A1 | 8/2006 | Romagne et al. |
| 2009/0208517 | A1 | 8/2009 | Moser et al. |

FOREIGN PATENT DOCUMENTS

| WO | WO2004085635 | 10/2004 |
| WO | WO2006/017954 | 2/2006 |

OTHER PUBLICATIONS

Abstract of Wheeler (Salud p'ublica de M'exico, (Jul.-Aug. 1997) 39 (4) 283-7).*
Efferson et al (Anticancer research, 2005, vol. 25, pp. 715-724).*
Bachman et al (Journal of Immunology, 2005, vol. 175, pp. 4677-4685).*
Burgdorf and Kurts (Current Opinion in Immunology, 2008, vol. 20, pp. 89-95).*
Bieback et al (Journal of General Virology, 2003, vol. 85, pt. 5, pp. 1179-1188).*
Malkovska et al (Cancer Research, 1992, vol. 52, pp. 5610-5616).*
Gossman et al (J Med Chem, 2002, vol. 45, pp. 4868-4874).*
Das et al (Immunity, 2001, vol. 15, pp. 83-93).*
Hintz et al (FEBS Letters, 2001, vol. 509, pp. 317-322).*
Caccamo, Nadia et al: "CXCR5 Identifies a subset of Vgamma9Vdelta2 T cells which secrete IL-4 and IL-10 and help B cells for antibody production" Journal of Immunology. vol. 177, 2006, pp. 5290-5295.
Brandes, Marlene et al: "Professional antigen-presentation function by human gamma delta T cells" *Science* (Washington DC). vol. 309, No. 5732, Jul. 2005, pp. 264-268.
Modlin, Robert et al: "Immunology. Now presenting: gamma delta T cells." *Science*. vol. 309, No. 5732, Jul. 8, 2005, pp. 252-253.
Takamatsu, H-H et al: "A sub-population of circulating porcine gamma delta T cells can act as professional antigen presenting cells" Veterinary Immunology and Immunopathology, vol. 87, No. 3-4, Sep. 10, 2002, pp. 223-224.
Collins, Robert A et al: "Gamma delta T cells present antigen to CD4+ alpha beta T cells" Journal of Leukocyte Biology, vol. 63, No. 6, Jun. 1998, pp. 707-714.
Morita, C T et al: "Direct presentation of nonpeptide prenyl pyrophosphate antigens to human gamma delta T cells." Immunity. vol. 3, No. 4, Oct. 1995, pp. 495-507.
Lanzavecchia, A et al: "T cells can present antigens such as HIV GP120 targeted to their own surfaces molecules" Nature (London), vol. 334, No. 6182, 1988, pp. 530-532.
Brandes, Marlene et al: "Flexible migration program regulates gamma delta T-cell involvement in humoral immunity." Blood vol. 102, No. 10, Nov. 15, 2003 pp. 3693-3701.
Lanzavecchia, A: "Receptor-mediated antigen uptake and its effect on antigen presentation to class II-restricted T Lymphocytes" Annual Review of Immunology, Annual Reviews INC, US, vol. 8, 1990, pp. 773-793.
www.bloodjournal.org; "Flexible migration program regulates γδ T-cell involvement in humoral immunity"; Blood Nov. 15, 2003, vol. 102, No. 10; pp. 3693-3701; © The American Society of Hematology; Marlene Brandes, Katharina Willimann, Alois B. Lang, Ki-Hoan Nam, Chenggang Jin, Michael B. Brenner, Craig T. Morita, and Bernhard Moser.

(Continued)

*Primary Examiner* — Karen A Canella
(74) *Attorney, Agent, or Firm* — King & Schickli, PLLC

(57) ABSTRACT

The invention relates to a method for the preparation of efficient antigen-presenting human γδ T cells, to the γδ T cells prepared by such a method, and to their use in immunotherapy, vaccination, vaccine development and diagnostics. Similar to dendritic cells (DCs) in potency and efficacy, these human γδ T cells process antigens and present antigenic peptides to αβ T cells and induce antigen-specific responses (proliferation and differentiation) in naïve αβ T cells. γδ T cells are easily purified from peripheral blood, acquire "maturation" status (expression of essential adhesion, co-stimulatory and major histocompatibility complex molecules) within 1 day of in vitro culture under stimulation and induce strong primary and secondary T helper cell and cytotoxic T cell responses. The γδ T cells may be used in a method of treatment of tumors or chronic or recurrent infectious diseases, in identification of novel tumor or pathogen-derived antigens, and in the diagnosis of the immune competence of a patient.

6 Claims, 20 Drawing Sheets

OTHER PUBLICATIONS

Office Action issued Jun. 24, 2010 in U.S. Appl. No. 12/271,576.
U.S. Appl. No. 12/271,576 Office Action dated Oct. 11, 2011.
U.S. Appl. No. 12/271,576 Office Action dated Nov. 24, 2010.
U.S. Appl. No. 12/433,030 Office Action dated Oct. 18, 2011.
U.S. Appl. No. 12/433,030 Office Action dated Apr. 27, 2011.
Moser (Trends in Immunology, Mar. 2006, vol. 27, pp. 112-118).
Hara et al (Journal of Ciinical Investigation, vol. 90 pp. 204-210), 1992.
Yamanaka et al (Clinical Cancer Research 2005 vol. 11 pp. 4160-4167).

* cited by examiner

PREPARATION OF ANTIGEN-PRESENTING HUMAN GAMMA-DELTA T CELLS AND USE IN IMMUNOTHERAPY

FIELD OF THE INVENTION

The invention relates to a method for the preparation of efficient antigen-presenting human γδ T cells, to the γδ T cells prepared by such a method, and to their use in immunotherapy, antigen identification and diagnosis of immune competence.

BACKGROUND OF INVENTION

The Cellular Components of the Adaptive Immune System

The cellular components of the immune system are divided into the cells of the innate immune system and the cells of the adaptive (acquired or specific) immune system. Cells of the innate immune system include (among others) monocytes, granulocytes, natural killer cells in peripheral blood, and mast cells, macrophages and dendritic cells (DCs) in extravascular compartments including peripheral tissues, such as skin, airways, gastrointestinal and urogenital tracts, internal organs as well as secondary lymphoid tissues, such as spleen, lymph nodes (LNs) and Peyer's patches (PPs). The main functions of innate cells are a) provision of immediate protection by neutralizing and limiting dissemination of infectious particles, and by tumor cell clearing, b) immune surveillance of healthy tissues, and c) initiation of adaptive immune responses. Cells of the adaptive immune system include lymphocytes, such as T and B cells. They are distinguished from innate cells by the presence of clonotypic cell surface antigen receptors, referred to as T cell antigen receptor (TCR) and B cell antigen receptor (BCR). Each individual lymphocyte carries a distinct TCR or BCR that recognizes a particular antigen. The specificity of antigen recognition is determined by rearrangement of multiple variable TCR or BCR gene segments during T and B cell development and during antigen affinity maturation at the time of effector T and B cell generation. Naïve, antigen-inexperienced T cells in peripheral blood differ from each other in the antigen-selectivity of their TCRs, and individual naïve T cells become expanded in response to immune activation by agents containing the antigen they are specific for. Consequently, during adaptive immune responses a set of naïve T cells with TCRs specific for the potentially infectious agent becomes expanded via cell proliferation, and develops into a) effector T cells for immediate participation in the defence against the potentially infectious agent, and into b) memory T cells for long-lasting protection against this particular potentially infectious agent. Effector T cells are short-lived, i.e. disappear during the resolution phase of the immune response, whereas the memory T cells are long-lived and are divided into memory T cell subsets according to their primary tissue residence or preferential recirculation routes (Moser et al., 2004). T cells are further divided into αβ T cells and γδ T cells (see below) according to the composition of the heterodimeric TCRs; αβ-TCRs are composed of α- and β-protein chains, and γδ-TCRs are composed of γ- and δ-protein chains. The majority (>80%) of all $CD3^+$ T cells in a normal, healthy person are αβ T cells. TCRs are associated with the invariant CD3 molecule that distinguishes T cells from B cells and all other types of immune cells. The majority of αβ T cells recognizes the antigen in a so-called major histocompatibility complex (MHC) molecules-restricted fashion. This is in contrast to BCRs in B cells that directly bind the nominal antigen in a MHC-non-restricted fashion. The term MHC-restriction refers to the mode by which the TCRs recognize their antigens and involves the presentation of antigenic peptides together with MHC molecules, as so-called MHC-peptide complexes, on antigen-presenting cells (APCs), including DCs (see below). There are two major classes of MHC molecules, MHC class I (MHC-I) and MHC class II (MHC-II), which trigger the TCRs of the two major subsets of αβ T cells, the $CD8^+$ αβ T cells and $CD4^+$ αβ T cells. The TCRs on $CD4^+$ αβ T cells recognize MHC-II-peptide complexes whereas the TCRs on $CD8^+$ αβ T cells recognize MHC-I-peptide complexes. In striking contrast, the major subset of γδ T cells in human peripheral blood does not express CD4 or CD8 and its TCRs do not require MHC-restriction for antigen recognition (see below).

γδ Cells

γδ T cells are a distinct subset of $CD3^+$ T cells featuring TCRs that are encoded by Vγ- and Vδ-gene segments (Morita et al., 2000; Carding and Egan, 2002). They are further divided according to their primary residence in blood or tissues, the protein chain composition of their VγVδ-TCRs and their antigen selectivity. In humans, $Vγ1^+$-TCR chain expressing γδ T cells ($Vδ1^+$ T cells) predominate in epithelial or epithelia-associated/mucosal tissues of the skin, airways, digestive and urogenital tracts, and several internal organs, and constitute a minor fraction (<20%) of γδ T cells in peripheral blood. The TCRs of $Vδ1^+$ T cells recognize lipid antigens presented by MHC-related CD1 molecules. Further, $Vδ1^+$ T cells respond to stress-associated proteins, including MHC-related molecules MICA and MICB, and heat-shock proteins. They are thought to provide a first-line defence against tumors and otherwise stressed cells and, in addition, are thought to contribute to wound healing, tissue repair and autoimmunity. In human peripheral blood of healthy individuals γδ T cells make up 2-10% of total $CD3^+$ T cells, and the majority (>80%) of peripheral blood γδ T cells are $Vγ2Vδ2^+$-TCR chain-expressing γδ T cells ($Vγ2Vδ2^+$ γδ T cells) (Morita et al., 2000; Carding and Egan, 2002). They are highly selective for small non-peptide antigens of mostly microbial origin and do not require antigen presentation by classical MHC molecules, as is typical for peptide-selective αβ T cells (see above). $Vγ2Vδ2^+$ γδ T cell antigens include prenyl-pyrophosphates, such as isopentenyl pyrophosphate (IPP), alkyl-amines and metabolites of a newly discovered isoprenoid biosynthesis pathway found in most human microbial pathogens and commensal bacteria (Morita et al., 2000; Eberl et al., 2003). Some of these $Vγ2Vδ2^+$γδ T cell antigens, such as IPP and alkyl amines, are also released by necrotic tissue cells. The homologue of human $Vγ2Vδ2^+$γδ T cells, carrying homologous VγVδ-TCRs with selectivity for small non-peptide antigens of microbial origin, does also exist in higher primates, such as macaques, but does not exist in rodents, including mice and rabbits. It is not clear why the presence of $Vγ2Vδ2^+$γδ T cells is limited to higher primates but it could be speculated that they evolved to satisfy the special need for cellular protection against a distinct, species-specific selection of microbes. $Vγ2Vδ2^+$γδ T cells rapidly expand in response to the model antigen IPP or microbial extracts in vitro during tissue culture of peripheral blood $Vγ2Vδ2^+$γδ T cells, or in vivo during vaccination experiments in higher primates, such as macaques (Chen and Letvin, 2003). Also, microbial infections in humans are frequently associated with tremendous expansion of peripheral blood $Vγ2Vδ2^+$γδ T cells, reaching levels as high as >60% of total peripheral blood $CD3^+$ T cells. These findings support the notion that human $Vγ2Vδ2^+$γδ T cells play an important role in immune processes during microbial infections (Morita et al., 2000; Carding and Egan, 2002; Chen and Letvin, 2003). Their unique selectivity for non-peptide antigens that are commonly found in microbes, including pathogens and commensal bacteria, suggest that the TCRs in Vγ2Vδ2$^+$γδ T cells fulfill a similar function as toll-like receptors (TLR) that trigger activation and maturation of DCs and other APCs in response to diverse ligands of microbial origin. γδ T cells contribute to pathogen elimination by rapid secretion of chemokines that initiate the recruitment of cells of the innate immune system and proinflammatory cytokines (TNF-α, IFN-γ) that stimulate antigen-presenting cells and enhance bacterial killing by granulocytes, macrophages and NK cells (Morita et al., 2000; Carding and Egan, 2002; Chen and Letvin, 2003). They also express natural killer cell receptors for killing of infected or neoplastic tissue cells. These findings support the notion that γδ T cells primarily fulfill innate functions, although secretion of pro-inflammatory cytokines, such as TNF-α, is known also to contribute to local adaptive immune responses. On the other hand, evidence for direct involvement of γδ T cells in adaptive immune responses is not clear-cut. For instance, it is reported that CD1-restricted T cells induce maturing in DCs that present CD1-lipid complexes. Also, studies in mice demonstrated a not further explained role for γδ T cells in B cell responses, and human γδ T cells were shown to regulate B cell responses during in vitro co-cultures (Brandes et al., 2003). Finally, studies in macaques demonstrated that Vγ2Vδ2$^+$γδ T cells were able to mount in vivo memory responses to Mycobacterium bovis antigens (Chen and Letvin, 2003). Collectively, these findings provide evidence that γδ T cells are able to interact with cells of the adaptive immune system, such as B cells and DCs. Most of these immunomodulatory functions were attributed to cytokine production by γδ T cells or were left unexplained. Importantly, none of these findings support a role for γδ T cells in antigen presentation. Lymphocyte function is intimately related to the lymphocyte migration potential, as defined by the expression of chemokine receptors and adhesion molecules (Moser et al., 2004). Accordingly, αβ T cells are divided into a) naïve T cells expressing the LN-homing chemokine receptor CCR7 but lacking receptors for inflammatory chemokines, b) short-lived effector T cells bearing distinct combinations of chemokine receptors and inducible adhesion molecules that mirror the inflammatory conditions at the site of infection, and c) three subsets of resting, long-lived memory T cells. The distinction of T cell subsets according to their migration potential, i.e. their expression profile of cell surface chemokine receptors and adhesion molecules, correlates well with their state of differentiation and potential function in immune processes. Of note, the "profiling" of chemokine receptors and adhesion molecules is widely used for phenotypic and functional definition of leukocyte subsets, including DCs, and T and B cells (Moser et al., 2004). The migration properties of human peripheral blood γδ T cells differ strikingly from those of human peripheral blood αβ T cells (Brandes et al., 2003). Most notably, the majority (>80%) of Vγ2V2$^+$ γδ T cells (hereafter referred to as "γδ T cells") lacks CCR7 and, thus, is excluded from secondary lymphoid tissues, but features an inflammatory migration profile (Brandes et al., 2003). In clear contrast, the majority (>70%) of αβ T cells in peripheral blood express CCR7, which agrees with their continuous recirculation through secondary lymphoid tissues (spleen, LNs, PPs) where they scan APCs for the presence of the appropriate MHC-peptide complexes. In case of ongoing adaptive immune responses, a selection of αβ T cells becomes activated during contact with APCs presenting their cognate antigens and differentiates into CCR7-negative effector cells with inflammatory homing potential. By contrast, peripheral blood γδ T cells feature an inflammatory migration program for their immediate tissue mobilization in response to inflammatory chemokines produced at sites of infection. Upon activation, e.g. in response to microbial extract antigens or defined small non-peptide antigens (such as IPP), the migration profile in γδ T cells rapidly switches from an inflammatory to a LN-homing phenotype, as evidenced by downmodulation of receptors for inflammatory chemokines and induction of CCR7 (Brandes et al., 2003). By contrast to αβ T cells, γδ T cells are relatively rare in LNs, which agrees with their distinct mode of activation that is fully independent of MHC-restricting APCs present at these locations (Brandes et al., 2003). The frequency of γδ T cells is increased in disease-associated LNs (notably in germinal centers), suggesting that γδ T cells may contribute to the initiation of humoral (antibody) responses and possibly other adaptive immune processes.

Collectively, migration characteristics of human γδ T cells and their occasional presence in LNs suggest a role for these cells in the initiation of adaptive immune responses. However, this role is not further defined and there is no evidence that γδ T cells may function as antigen-presenting cells.

Dendritic Cells (DCs)

DCs form a distinct class of leukocytes, are derived from hematopoietic progenitor cells in the bone marrow, and primarily reside in extravascular sites that include epithelial/mucosal tissues (skin, airways and gastrointestinal/urogenital tracts, among others) and secondary lymphoid tissues (spleen, LNs, PPs) (Banchereau and Steinman, 1998; Steinman et al., 2003; Banchereau et al., 2004). In peripheral blood, DCs or DC precursors make up less than 1% of mononuclear leukocytes. Distinct DC subsets differ in their tissue localization, as exemplified by interstitial DCs that primarily reside in soft tissues bordering epithelia, Langerhans cells (LCs) present in the epidermis and plasmacytoid DCs with homing preferences for LNs. These DC subsets are fully differentiated non-proliferating cells with a limited life-span of several days to several weeks, indicating that they are continuously replaced under steady-state conditions by bone marrow-derived precursors. By contrast, human memory T cells survive for many years and are maintained by means of steady-state (homeostatic) proliferation. The principal function of tissue-resident DCs is the uptake and processing of local antigens, their relocation via afferent lymphatic vessels to draining LNs and the initiation of antigen-specific adaptive immune responses (Banchereau and Steinman, 1998; Steinman et al., 2003; Banchereau et al., 2004). DCs also induce tolerance when antigens are presented to T cells under tolerogenic conditions, i.e. in the absence of pro-inflammatory T cell co-stimulation. Similarly, antigen-presenting B cells have been shown to induce tolerance (Zhong et al., 1997). Break in the immunological tolerance against self-antigens is thought to be the frequent cause of autoimmune diseases and, thus, tolerogenic DCs presenting self-antigens are essential regulators of immune homeostasis. In healthy peripheral tissues DCs are present in their fully differentiated but "immature" state. Immature DCs express a set of receptors for inflammatory chemokines for quick recruitment to local infection, inflammation or tissue damage. They themselves are poorly immunogenic, i.e. are not capable of inducing primary adaptive immune responses. Instead they are experts in antigen uptake (by means of receptor-mediated endocytic or fluid phase pinocytic mechanisms), antigen processing and peptide loading onto intracellular MHC-I/II molecules and their cell surface presentation. Since immature DCs do not generally express the LN-homing receptor CCR7 it is not known at present how this type of DCs reaches the T cell areas in spleen, LNs and PPs. A multitude of maturation signals, including virus- or bacteria-derived stimuli that trigger toll-like receptors (TLRs), host cell-derived inflammatory mediators (interferon [IFN]-γ, tumor necrosis factor [TNF]-α, interleukin [IL]-1, prostaglandin E2 [PGE2], tissue growth factors, among others), and T cell co-stimulatory molecules (CD40-ligand/CD154), induce DC "maturation" (Banchereau and Steinman, 1998; Steinman et al., 2003; Banchereau et al., 2004). During the early phase of DC maturation, DCs secrete high levels of inflammatory chemokines for augmentation of the inflammatory response via recruitment of additional immature DCs and cells of the innate immune system (monocytes, granulocytes, natural killer cells). Subsequently, the inflammatory migration program is gradually substituted by a LN-homing migration program characterized by substitution of receptors for inflammatory chemokines with CCR7. CCR7 is essential for efficient relocation of sensitized DCs from peripheral tissues to draining LNs in response to the two CCR7-selective chemokines ELC/CCL19 and SLC/CCL21 present on lymphatic vessels and in the T cell area of spleen, LNs and PPs. Thus, CCR7 expression marks mature or maturing DCs. In addition to LN-homing properties, mature DCs feature stable cell surface expression of MHC-I/II-peptide complexes in large numbers as well as diverse co-stimulatory molecules that are required for proper stimulation of naïve (antigen-inexperienced) αβ T cells (Banchereau and Steinman, 1998; Steinman et al., 2003; Banchereau et al., 2004). DCs are also referred to as "professional" APCs because they are capable of stimulating naïve αβ T cells during primary immune responses. Memory (antigen-experienced) T cells have a lower activation threshold and, thus, respond to less stringent stimulatory regimens. The functional duality of DCs that distinguishes between the two states of differentiation, a) immature, antigen-processing DCs in peripheral tissues and b) relocated mature, antigen-presenting and co-stimulating DCs in the tissue-draining LNs, is a hallmark of DC physiology and is tightly linked to local inflammation, infection or tissue damage. Finally, the outcome (quality and quantity) of the adaptive immune response is largely determined by the "mode" of response initiation. DCs are known to "instruct" naïve T cells within the T cell area of LNs and PPs about the type of immune response required for pathogen elimination (Banchereau and Steinman, 1998; Steinman et al., 2003; Banchereau et al., 2004). Accordingly, the inflammatory environment in the tissue directly influences DC maturation and, due to DC relocation, also determines T cell differentiation within draining LNs. Distinct effector fates of naïve T cell differentiation include specialized subsets of T helper cells (IFN-γ/TNF-α-producing type 1 T helper [Th1] cells, IL-4/IL-5/IL-13-producing Th2 cells, among others), regulatory T cells and cytolytic T cells (CTLs). Effector T cells home to sites of inflammation, rapidly mount effector functions (cytokine secretion, lysis/killing of infected/tumor cells) and have a limited life-span. By contrast, memory T cells are the long-lived product of primary immunization and mount superior immune responses against recall antigens.

Dendritic Cells in Immunotherapy

DCs are "nature's adjuvant", i.e. constitute the most expert cellular system for induction of protective immune responses, and, therefore, are being developed for use in human immunotherapy (Fong and Engleman, 2000; Steinman et al., 2003; Schuler et al., 2003; Figdor et al., 2004). Potential applications include cancer therapy, vaccination against pathogens (such as human immunodeficiency virus [HIV]-1 and hepatitis C virus) and treatment of autoimmune diseases. Current DC therapy protocols include 1. Isolation and purification of DC precursors from patients' blood (bone marrow-derived $CD34^+$ hematopoietic precursors or peripheral blood $CD14^+$ or $CD11c^+$ cells).
2. Generation of DCs during in vitro cell culture.
3. In vitro antigen loading for peptide-presentation by mature DCs.
4. Treatment of patients with single or repeated injections of peptide-presenting DCs.

Currently, the application of DCs in immunotherapy faces several problems (Fong and Engleman, 2000; Steinman et al., 2003; Schuler et al., 2003; Figdor et al., 2004). In brief, DC precursors are scarce in peripheral blood and do not proliferate during in vitro culture, necessitating repeated manipulation with large blood samples from patients. DCs are functionally heterogeneous and may induce opposing or unwanted effects, e.g. immune suppression instead of effector T cell generation. Also, DCs are functionally instable and go through a preset sequence of irreversible differentiation steps ending in compromised ("exhausted") immune functions. This causes great difficulties in generating functionally homogeneous DC preparations by in vitro manipulations. Finally, the generation of peptide-presenting DCs for use in immunotherapy is technically demanding, time consuming and costly.

SUMMARY OF INVENTION

The present invention describes the simple isolation and in vitro preparation of antigen-presenting human γδ T cells and their use as efficient antigen-presenting cells (APCs) in immunotherapy. Similar to dendritic cells (DCs) in potency and efficacy, human γδ T cells process antigens and present antigenic peptides to αβ T cells and induce antigen-specific responses (proliferation and differentiation) in naïve αβ T cells. γδ T cells are relative frequent in peripheral blood (2-10% of $CD3^+$ T cells), are easily purified from peripheral blood by diverse simple techniques, acquire "maturation" status (expression of MHC-II, and essential adhesion and co-stimulatory molecules) within 1 day of in vitro culture under simple stimulatory conditions, maintain efficient antigen-presenting functions over 7 days or more of in vitro culture and induce strong primary and secondary T helper cell responses. Furthermore, γδ T cells are readily expanded during in vitro culture for storage and later use.

The invention relates to a method for the preparation of efficient antigen-presenting human γδ T cells comprising selecting γδ T cells out of human peripheral blood mononuclear cells, treating the selected cells with a stimulus for induction of antigen-presenting functions, and applying the antigen to these cells (either before, during or after induction of antigen-presenting functions), to the efficient antigen-presenting human γδ T cells prepared by such a method, their use in immunotherapy and in the manufacture of a medicament for use in immunotherapy, to a method of treatment of tumors or chronic or recurrent infectious diseases with such efficient antigen-presenting human γδ T cells, to a method of vaccination against tumors or agents inducing infectious or non-infectious diseases with γδ T cell-targeting vaccines and to the use of such γδ T cell-targeting vaccines in the preparation of a medicament, to a method of identification of novel tumor or pathogen-derived antigens, and to a method of diagnosing the immune competence of patients using such efficient antigen-presenting human γδ T cells.

Examination of cell surface molecules by flow cytometry is performed with γδ T cells (γδ T), either freshly isolated from peripheral blood or after stimulation with IPP and in vitro culture for 1 or 7 days, or with αβ T cells (αβ T) after 1 day stimulation with anti-CD3/CD28, or with freshly isolated peripheral blood monocytes (M). The numbers above the individual dot-blots refer to the time of in vitro culture; (0d) freshly isolated, (1d) 1 or (7d) 7 days. Positivity is defined by staining with isotype-matched control antibodies, and horizontal lines represent the gates for 99% background stainings.

Figure 2:
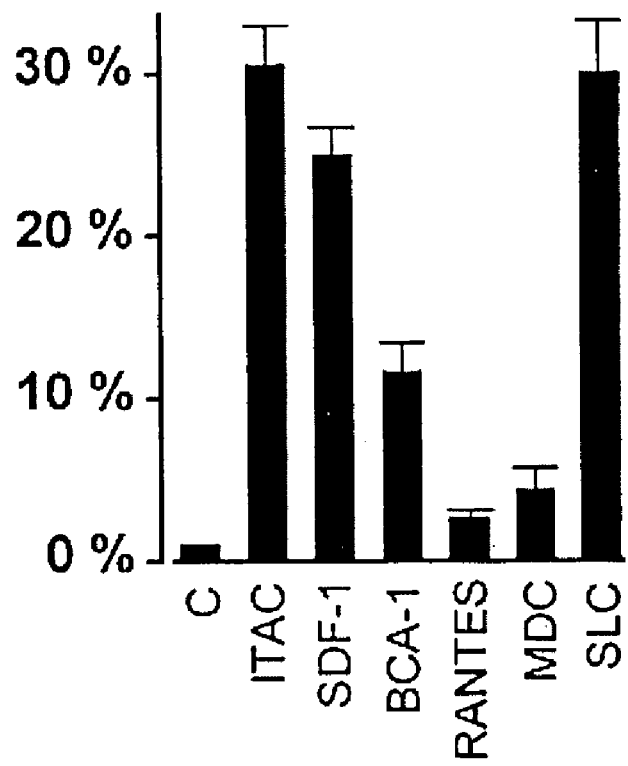
Figure 2:
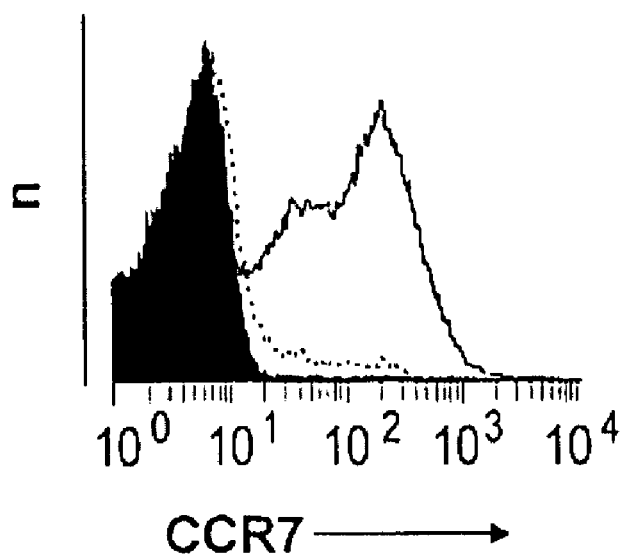

FIG. 2. Stimulated γδ T cells express functional CCR7 and respond to the LN chemokine SLC/CCL21.

The data are taken from Brandes et al., 2003. A) Chemotaxis responses are examined in γδ T cells after stimulation for 36 hours with IPP, and expressed as the fraction of cells (%), i.e. % of total input cells, that have migrated in response to the indicated chemokines. C=Control (blank). B) CCR7 expression is determined by flow cytometry, n=cell counts. Solid and broken lines refer to CCR7 expression on IPP-stimulated (see chemotaxis) and resting peripheral blood γδ T cells, respectively; filled histogram depicts control staining with isotype antibody.

Figure 3:
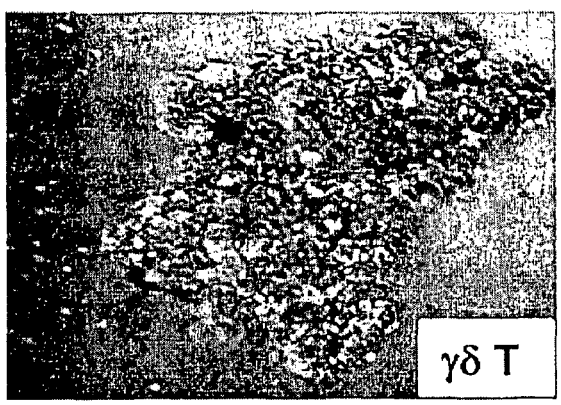
Figure 3:
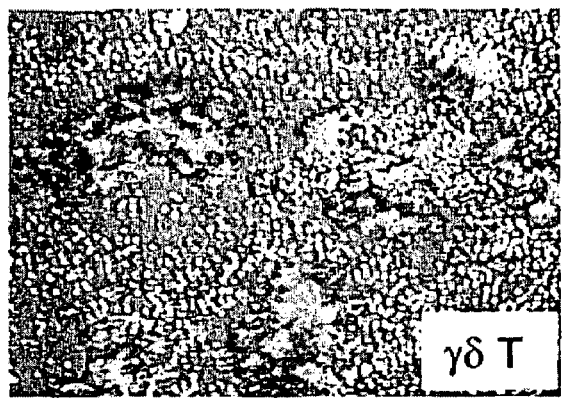
Figure 3:
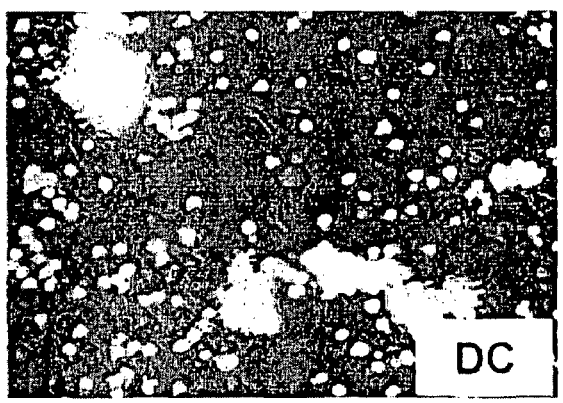
Figure 3:
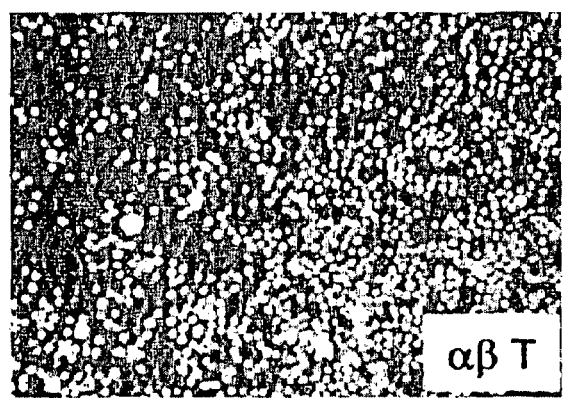

FIG. 3. Rapid and extensive aggregate formation between stimulated γδT cells and naïve αβ T cells.

1 day stimulated γδ T cells are cultured together with autologous, naïve CD4$^+$ αβT cells at the ratio of 1:5 for 3 hours (γδ T, 2 examples). As positive and negative control, mature monocyte-derived DCs (DC) and 1 day stimulated αβ T cells (αβ T), respectively, are mixed with autologous naïve αβ T cells. All cells are isolated from the same donor to exclude antigenic interactions. Naïve CD4$^+$ αβ T cells are loaded with CFSE for identification by fluorescence microscopy. The phase-contrast and fluorescence images of live cells are taken with a Zeiss-Axiovert 35 inverted microscope and images are combined in overlays.

Figure 4:
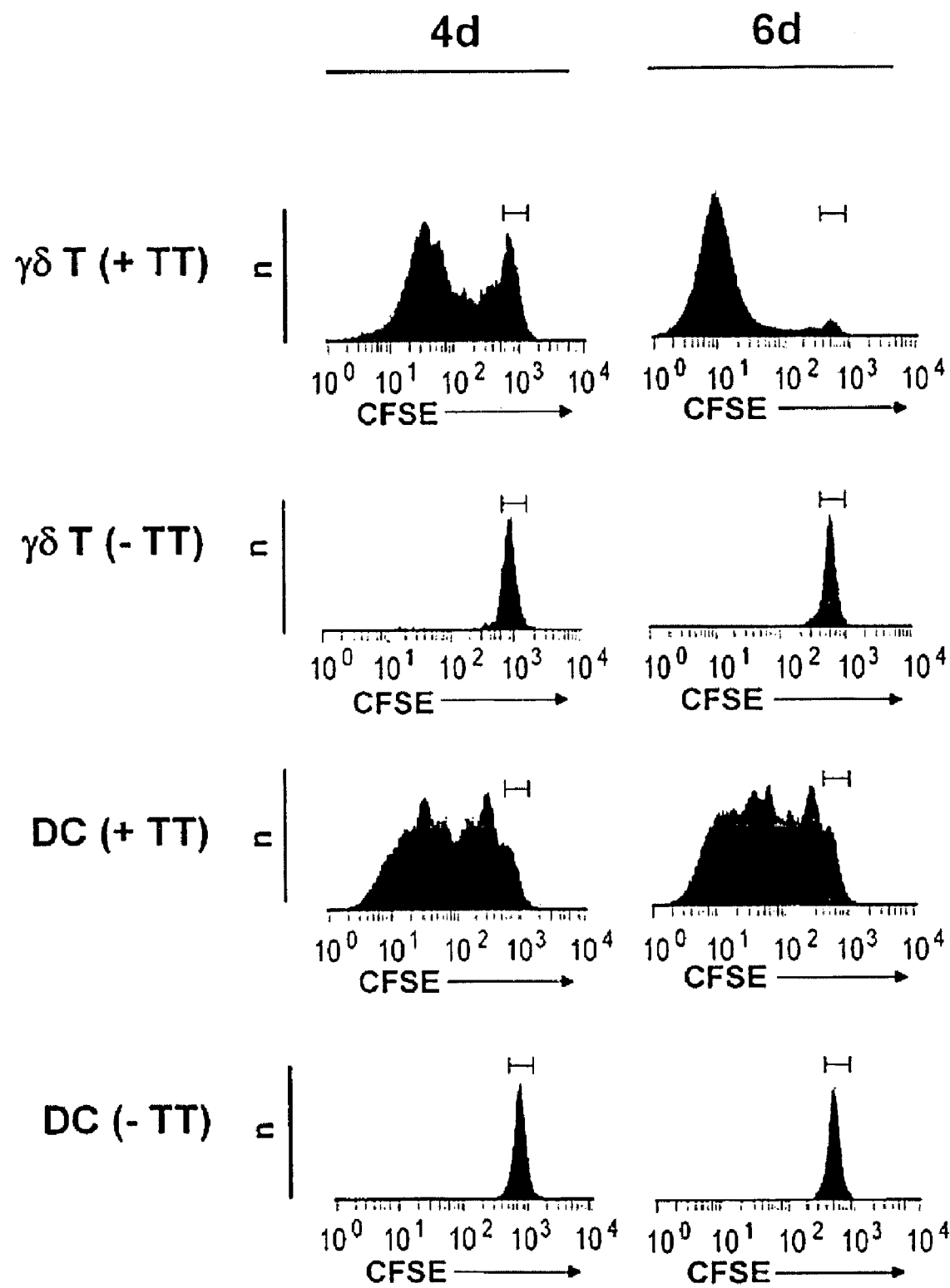

FIG. 4. Stimulated γδ T cells induce potent TT-specific proliferation responses in resting CD4$^+$ αβ T cells.

γδ T cells are stimulated for 1 day in the presence of 20 gg/ml TT, washed and then added to CFSE-labeled TT-specific αβ T cells at a ratio of 1:2. After 4 (4d) and 6 (6d) days of culture, the CFSE signals in CD4$^+$ cells are examined by flow cytometry (γδT(+TT)). As a positive control, monocyte-derived DCs are matured in the presence of 20 μg/ml TT (DC(+TT)) and used to stimulate αβ T cells at a ratio 1:10 under the same conditions as TT-presenting γδ T cells. As negative control, αβ T cells are co-cultured with γδ T cells (γδT(-TT)) and DCs (DC(-TT)), which are stimulated and matured, respectively, in the absence of TT. The horizontal bars above histograms indicate the positions of CFSE signals in undivided (non-responsive) cells; n=cell counts.

Figure 5:
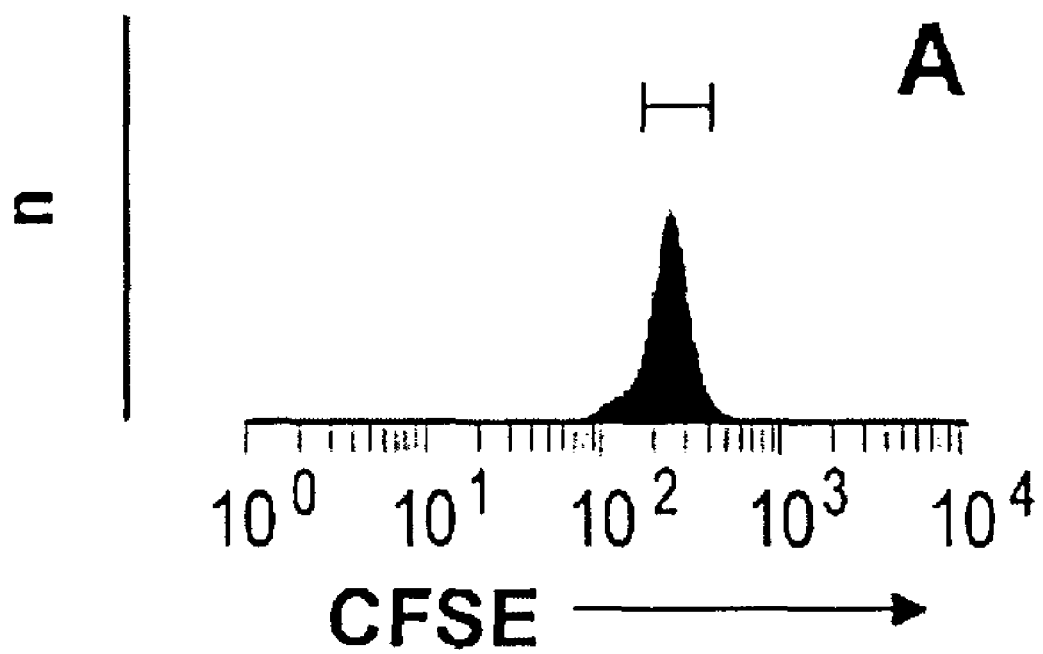
Figure 5:
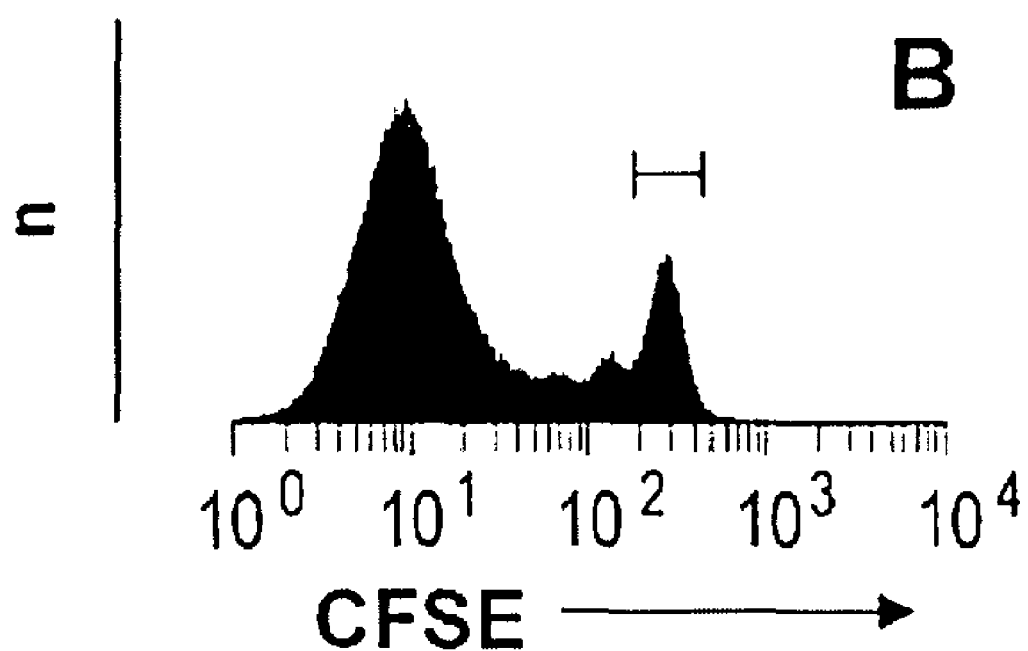

FIG. 5. Proliferation of TT-specific CD4$^+$ αβ T cells requires contact with TT-presenting γδ T cells.

Preparation of TT-presenting γδ T cells and CFSE-labeled responder cells as well as data analysis are performed exactly as described in FIG. 4. In a two-chamber tissue culture system, TT-presenting γδ T cells and TT-specific responder (CD4$^+$ αβ$^+$ T) cells are added to the lower chamber (B), and responder cells alone are added to the upper chamber (A). The two chambers are separated by a porous membrane allowing the free exchange of soluble proteins but not intact cells. Horizontal bars above histograms indicate the gates for undivided CFSE-labeled cells.

Figure 6:
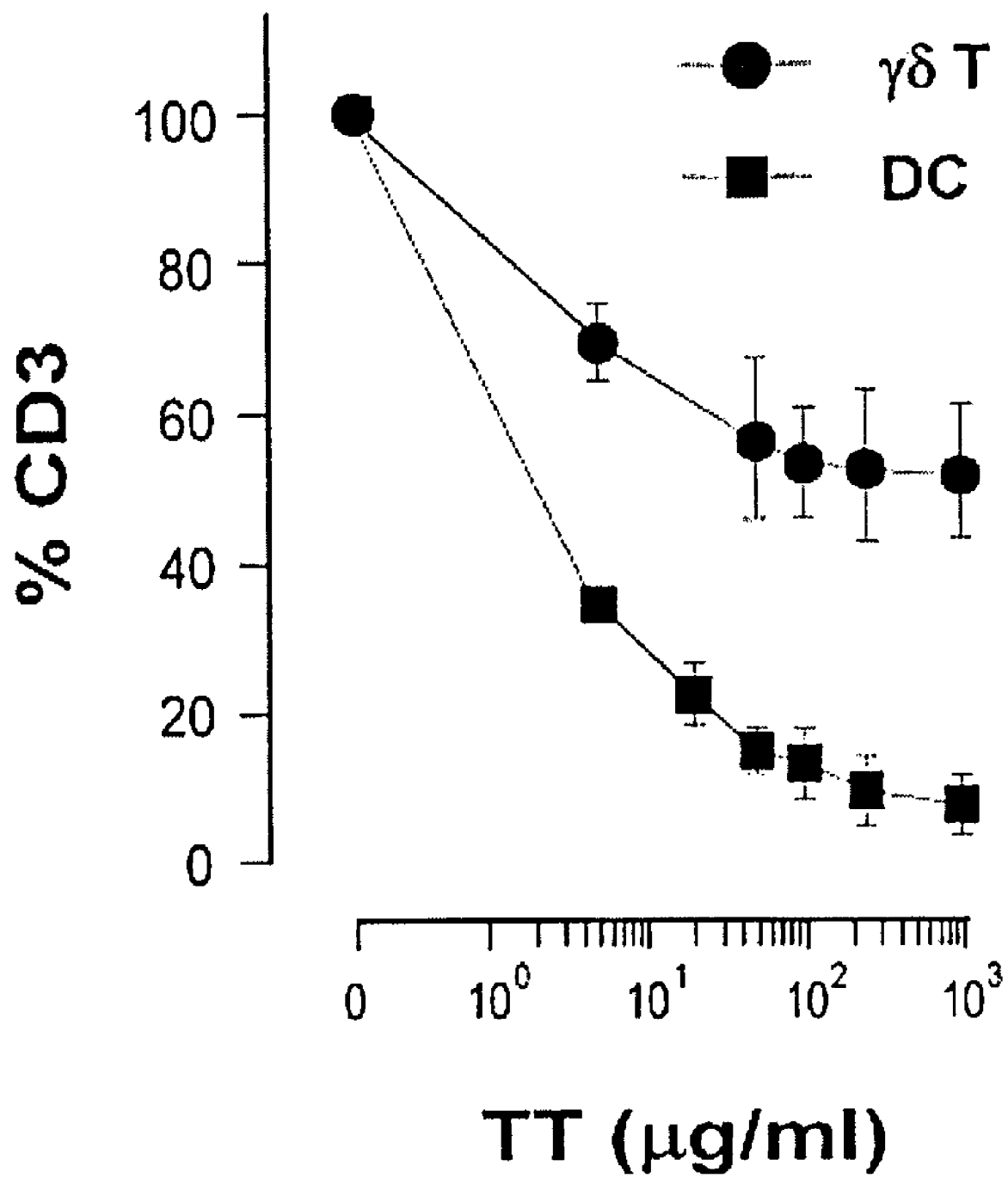

FIG. 6. TT-presenting γδ T cells induce TCR down-modulation in TT-specific CD4$^+$ αβ T cells.

γδ T cells and DCs are stimulated and matured, respectively, in the presence of increasing concentrations of TT, ranging from 0 (no TT added) to 1'000 μg/ml and then cultured with resting TT-specific CD4$^+$ αβ T cells at a APC: responder cell ratio of 1:2. After 18 hours, the level of CD3 expression on αβ T cells is determined by flow cytometry and shown in % of mean fluorescence intensity (MFI) compared to cells without TT added. Preparation of TT-presenting γδ T cells and responder cells as well as data analysis are performed exactly as described in FIG. 4.

Figure 7:
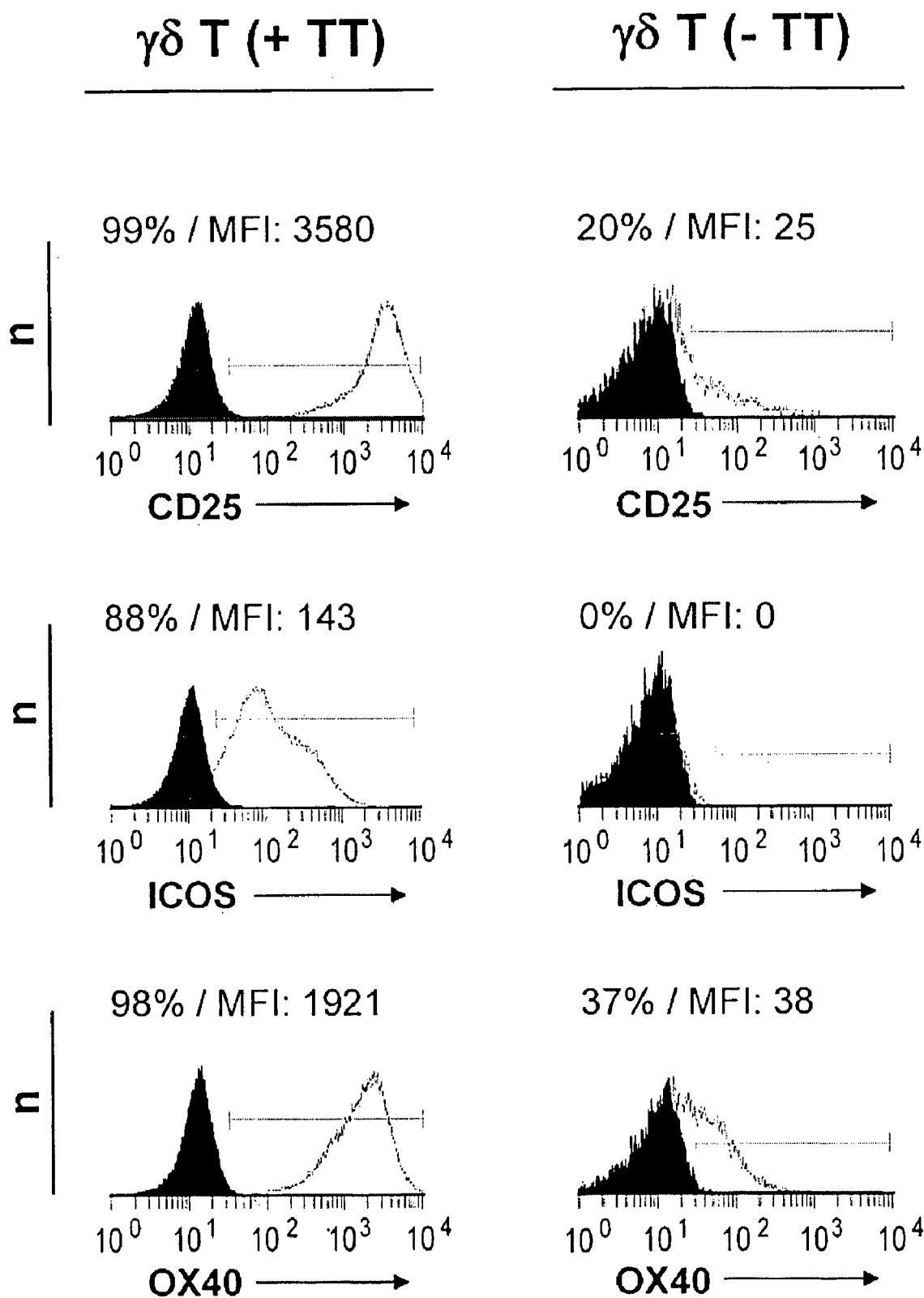

FIG. 7 TT-presenting γδ T cells induce the expression of activation markers on TT-specific CD4$^+$ αβ T cells.

The level of the activation markers CD25, ICOS and OX40 on TT-specific CD4$^+$ αβ T cells (responder cells) is determined by flow cytometry after culture for 5 days with γδ T cells that are stimulated in the presence (+TT) or absence (−TT) of 10 μg/ml TT (see FIG. 4). Open and filled histograms show the fluorescence stainings with specific and control isotype antibodies, respectively; n=cell counts. Horizontal bars represent the gates for marker-positive cells, and the numbers above the histograms indicate the degree of positivity, expressed as percent positive cells (%) and mean fluorescence intensity (MFI).

Figure 8:
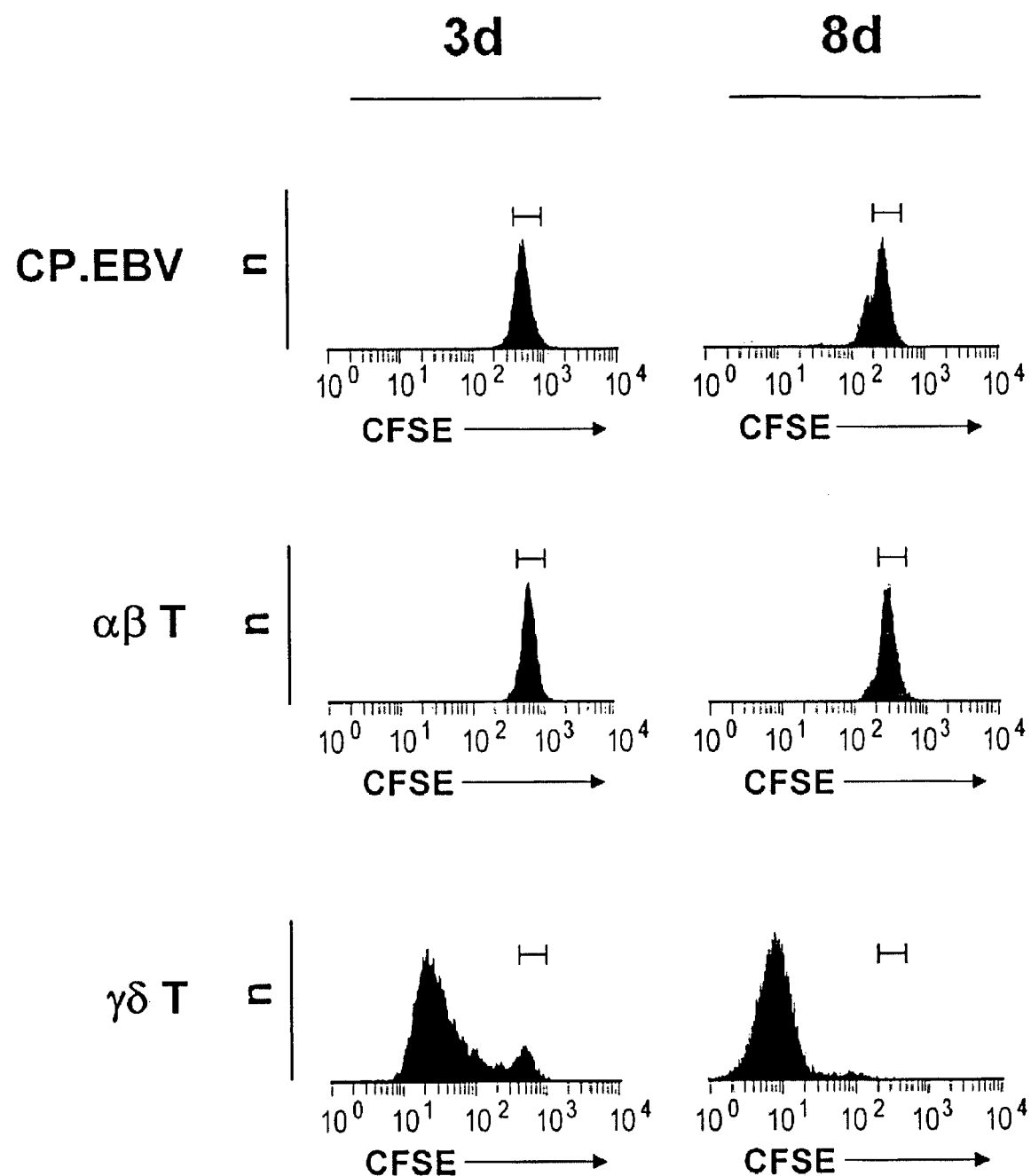

FIG. 8. Heterologous EBV-B cells and TT-specific CD4$^+$ αβ T cells do not functionally present TT to TT-specific responder cells.

CP.EBV cells, responder cells (TT-specific CD4$^+$ αβ T cells) and γδ T cells (as positive control) are cultured for 1 day in the presence of 20 μg/ml TT, washed, irradiated and then added to TT-specific CD4$^+$ αβ T cells at a ratio of 1:2. After 3 (3d) and 8 (8d) days of culture, the CFSE signals in CD4$^+$ cells are examined by flow cytometry. CP.EBV and responder cell preparation, CFSE-labeling and flow cytometry are described in "Examples".

Figure 9:
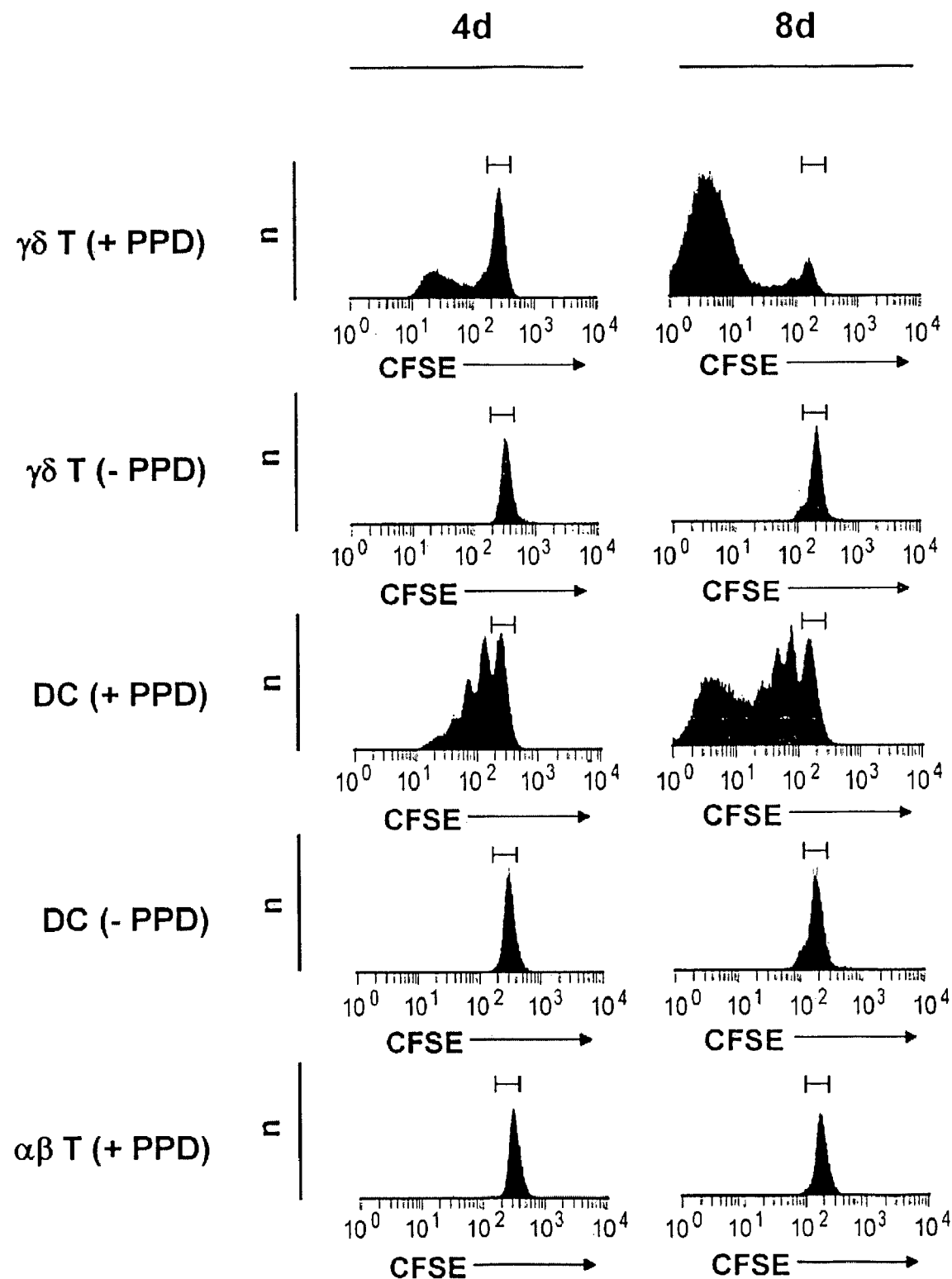

FIG. 9. Stimulated γδ T cells are also efficient in processing and presenting complex protein antigens (PPD).

γδ T cells and DCs are stimulated/matured in the presence (+PPD) or absence (−PPD) of 20 μg/ml PPD and analyzed for induction of proliferation in resting autologous PPD-specific CD4$^+$ αβ T cells. As additional negative control, PPD-specific CD4$^+$ αβ T cells are cultured in the absence of γδ T cells or DCs but in the presence of 20 μg/ml PPD. The experimental set-up is identical to the one used in FIG. 4. γδ T cells and DC preparation, CFSE-labeling of PPD-specific CD4$^+$ αβ T cells and flow cytometry are described in "Examples".

Figure 10:
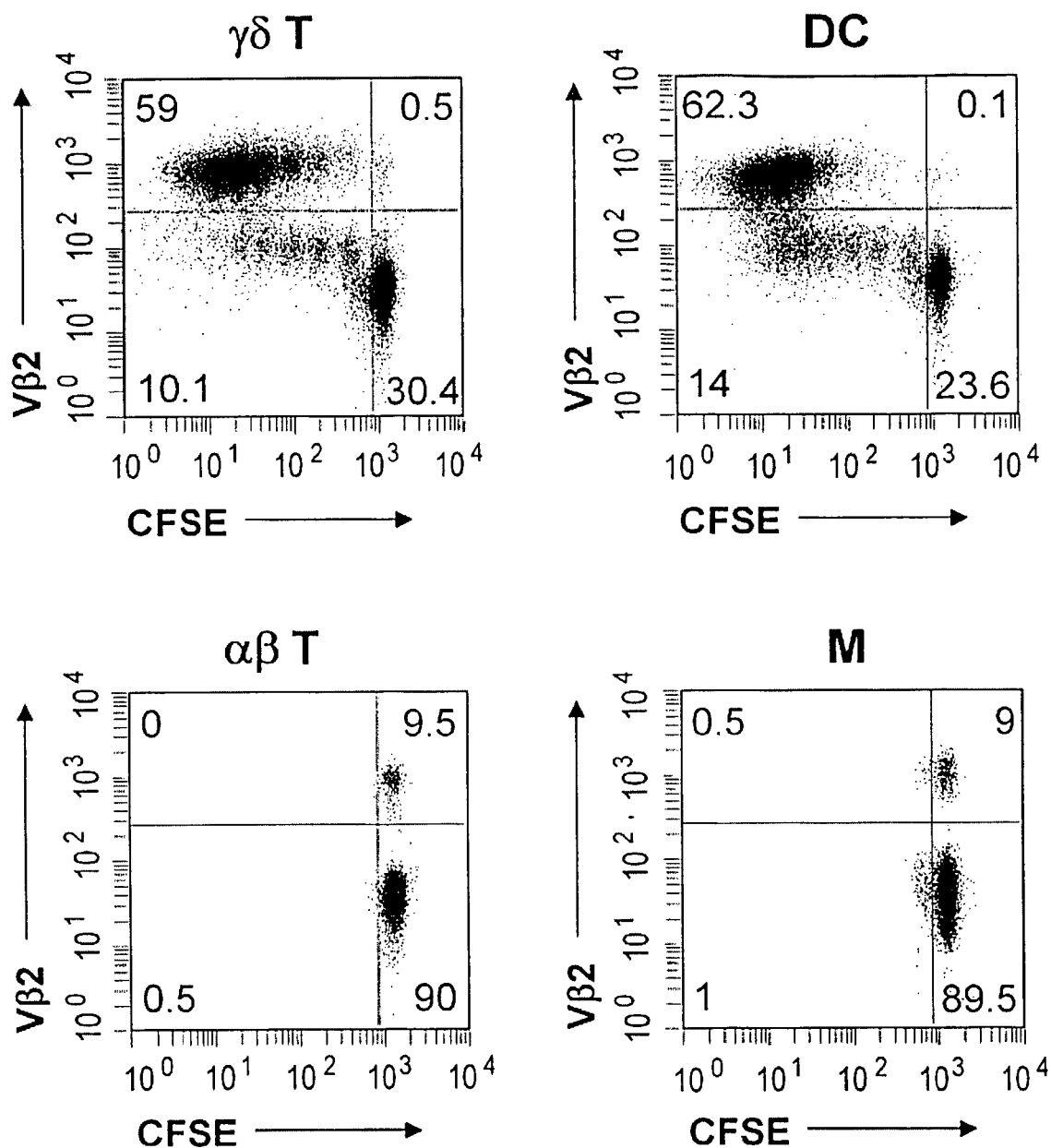

FIG. 10. TSST-1-loaded γδ T cells induce proliferation in autologous naïve CD4$^+$ αβ T cells.

Stimulated γδ T cells (γδ T), stimulated CD4$^+$ αβ T cells (αβ T), mature DCs (DC) and freshly isolated blood monocytes (M) are loaded with 10 ng/ml TSST-1 and mixed with freshly isolated, CFSE-labeled naïve CD4$^+$ αβ T cells at a ratio of 1:5. After 4 days of culture the proliferation responses in Vβ2$^+$-αβ T cells (Vβ2) are determined by flow cytometry. Vertical and horizontal lines in the dot-blots define the gates for Vβ2$^+$-αβ T cells and divided cells; the left-upper and left-lower quadrants show divided Vβ2$^+$-cells and divided Vβ2$^{neg}$-cells, respectively, and the right-upper and right-lower quadrants show undivided Vβ2$^+$-cells and undivided Vβ2$^{neg}$-cells; the numbers refer to the percent of total cells present within the individual quadrants. Cell preparation, TSST-1-loading and flow cytometry are performed according to "Examples".

Figure 11:
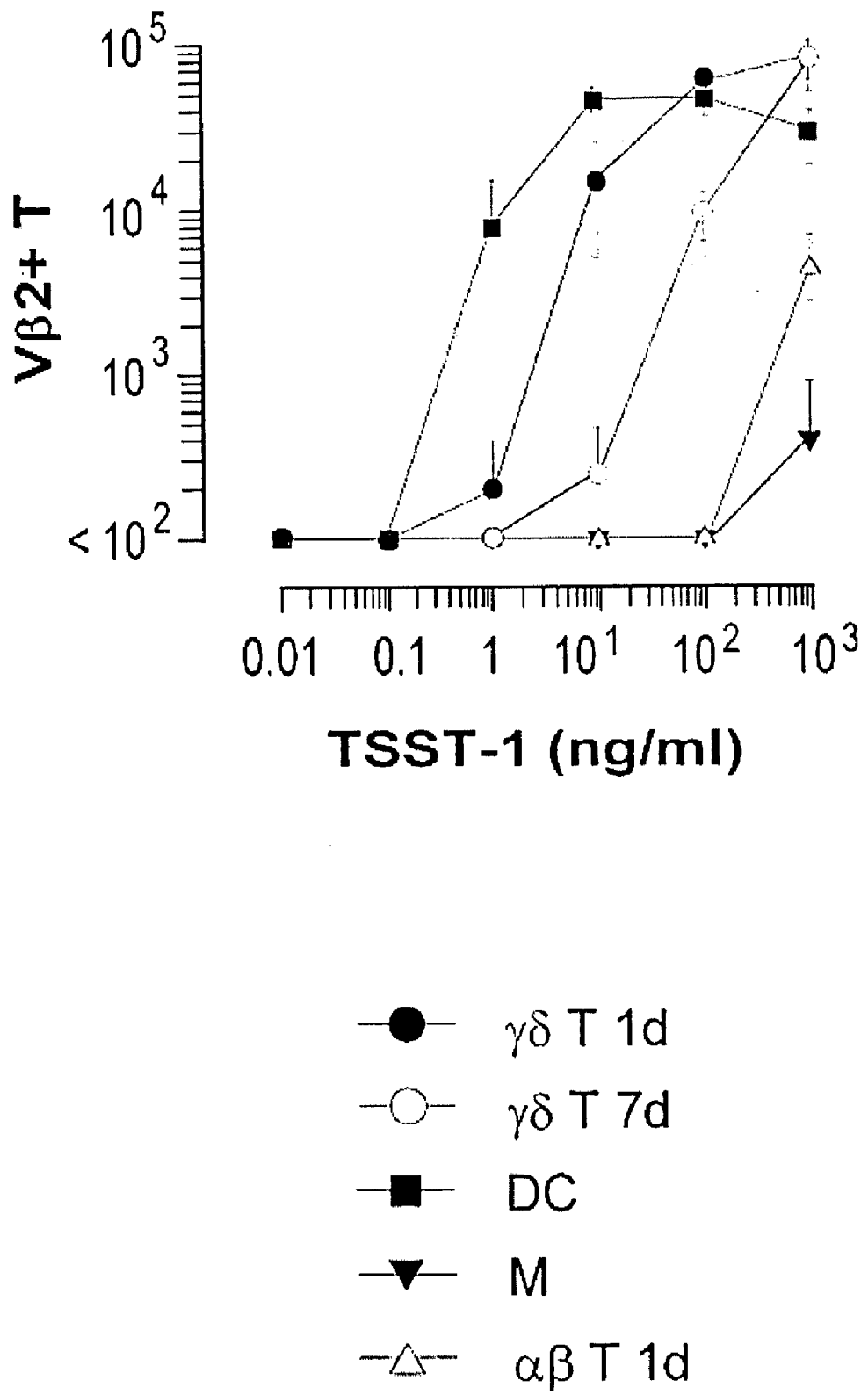

FIG. 11. TSST-1-loaded γδ T cells demonstrate potent APC functions (titration of TSST-1).

Stimulated γδ T (γδ T) and αβ T cells (αβ T), dendritic cells (DC) and monocytes (M) are loaded with increasing concentrations of TSST-1 and mixed with CFSE-labeled naïve CD4$^+$ αβ T cells at a ratio of 1:5. After 4 days of culture the number of divided Vβ2$^+$-αβ T cells per culture well (Vβ2+ T) are determined by flow cytometry (see upper-left quadrants in FIG. 10). The antigen-presenting cells tested are those shown in FIG. 10 and, in addition, stimulated γδ T cells that are cultured for 7 days and then loaded with varying concentrations of TSST-1 (γδ T 7d). Each data point plus error bar represents the mean ±standard deviation (SD) of duplicate values from 2 separate experiments and data are representative of 3 independent experiments. Cell preparation, TSST-1 -loading and flow cytometry are performed according to "Examples".

Figure 12:
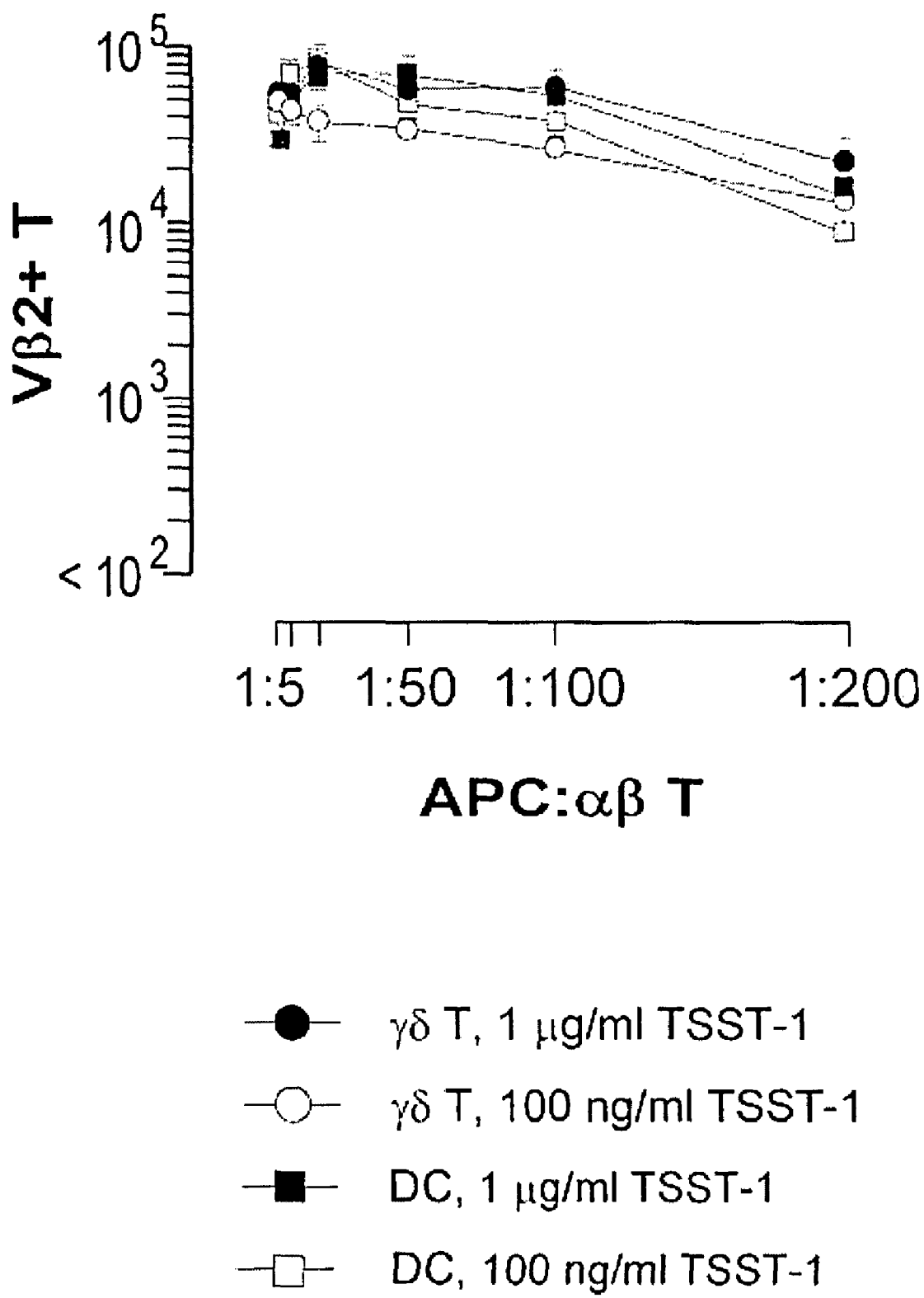

FIG. 12. TSST-1-loaded γδ T cells demonstrate potent APC functions (titration of APCs).

Stimulated γδ T cells and mature DCs are loaded with either 1 μg/ml or 100 ng/ml TSST-1 and tested at various dilutions (1:5 to 1:200) of APC:αβ T cells (APC: γδ T cells or mature DCs) for induction of proliferation in naïve CD4+ αβ T cells. Cell preparation, TSST-1-loading and flow cytometry are performed according to "Examples".

Figure 13A:
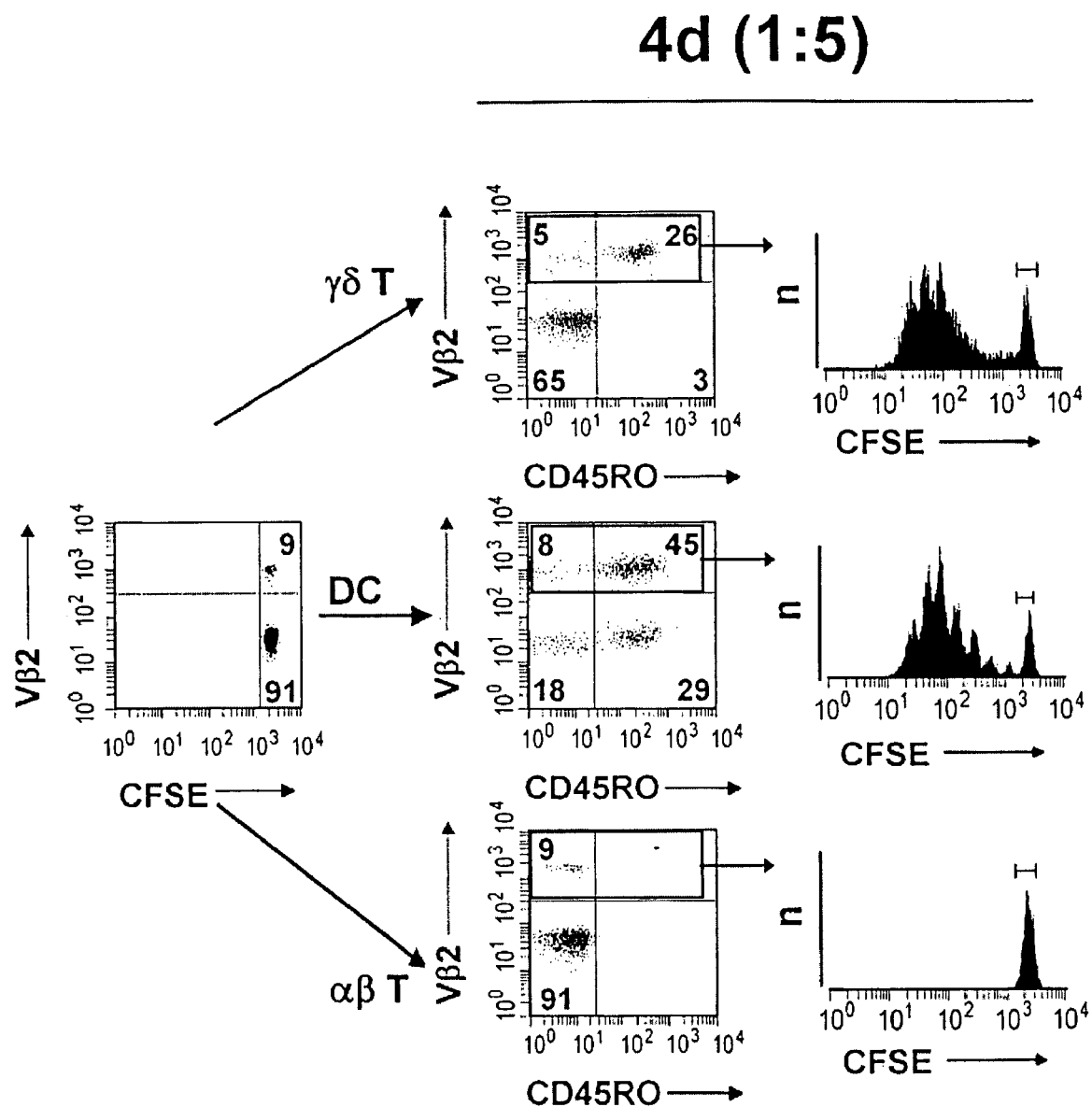
Figure 13B:
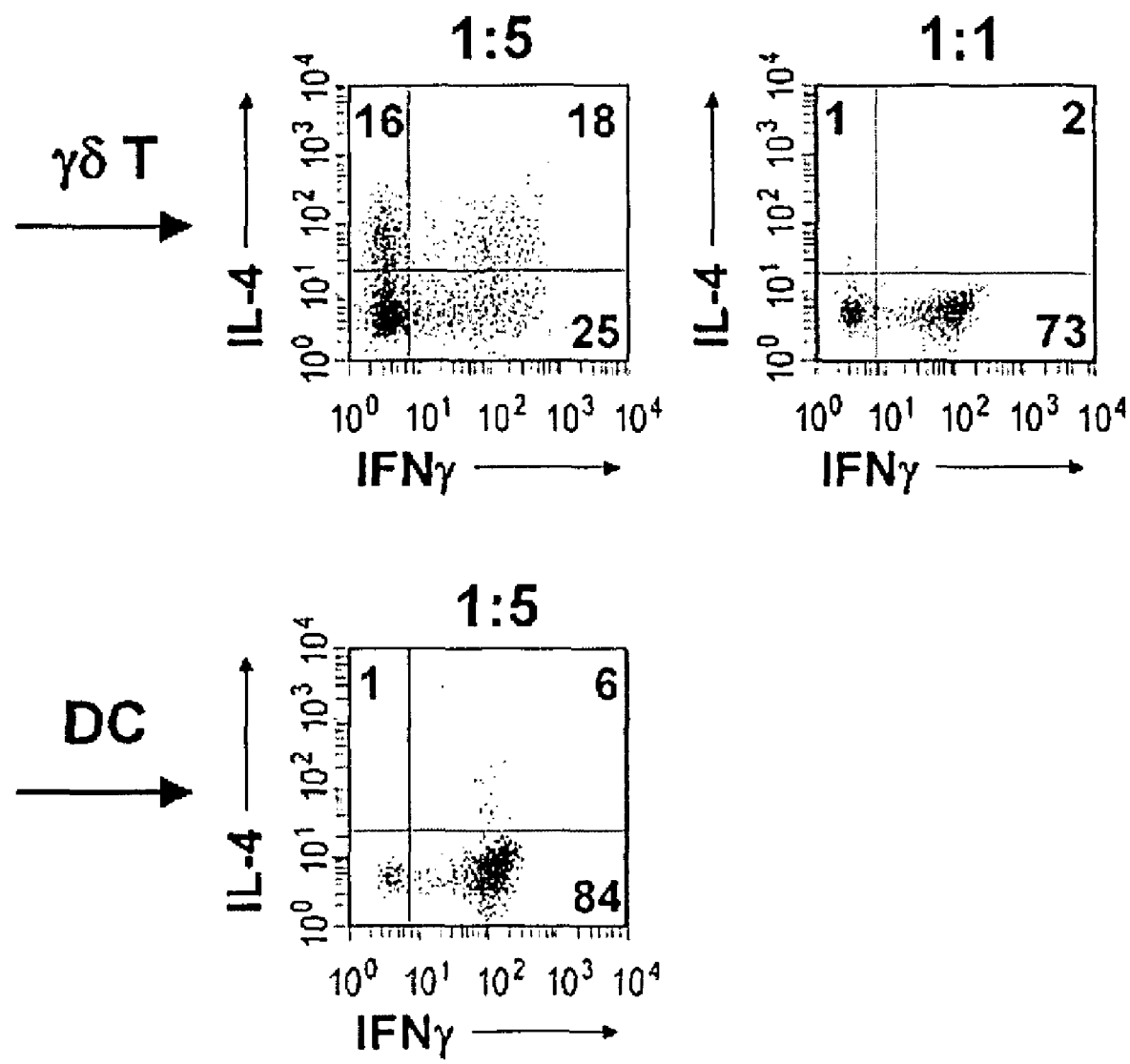

FIG. 13 (13A and 13B). TSST-1-loaded γδ T cells induce T helper cell differentiation in naïve CD4+ αβ T cells.

Stimulated γδ T cells, αβ T cells or mature DCs loaded with 10 ng/ml TSST-1 are mixed with naïve CD4+ αβ T cells, and Vβ2+ responder cell proliferation is examined as described in FIG. 10. After 4 days of culture, expression of the memory marker CD45RO and the extent of cell division are determined by flow cytometry in Vβ2+ responder cells. After 21 days of culture, when the cells return to a resting, non-proliferating state, cells are stimulated by PMA/ionomycin and examined by flow cytometry for the production of the intracellular cytokines IL-4 and IFN-γ (FIG. 13 B). The numbers in the left-upper, right-upper and right-lower quadrants define the fraction (percent of total cells) of Th2, Th0 and Th1 cells generated, respectively, and the numbers above the individual dot-blots refer to the ratio of APCs to responder cells at the beginning of the cell cultures. Cell preparation, TSST-1-loading and determination of cytokine production are described in "Examples".

Figure 14:
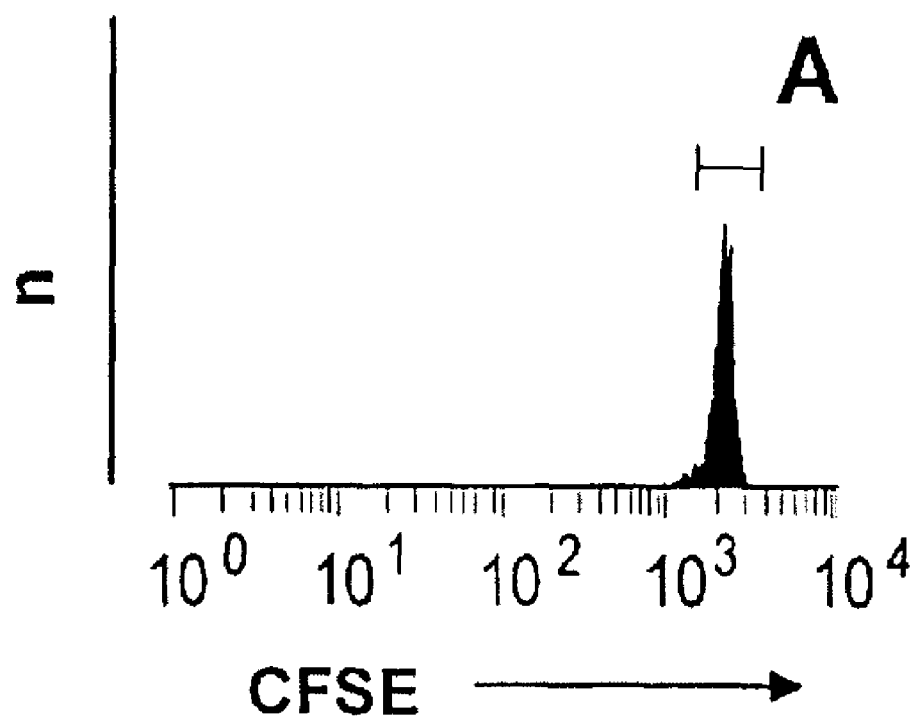
Figure 14:
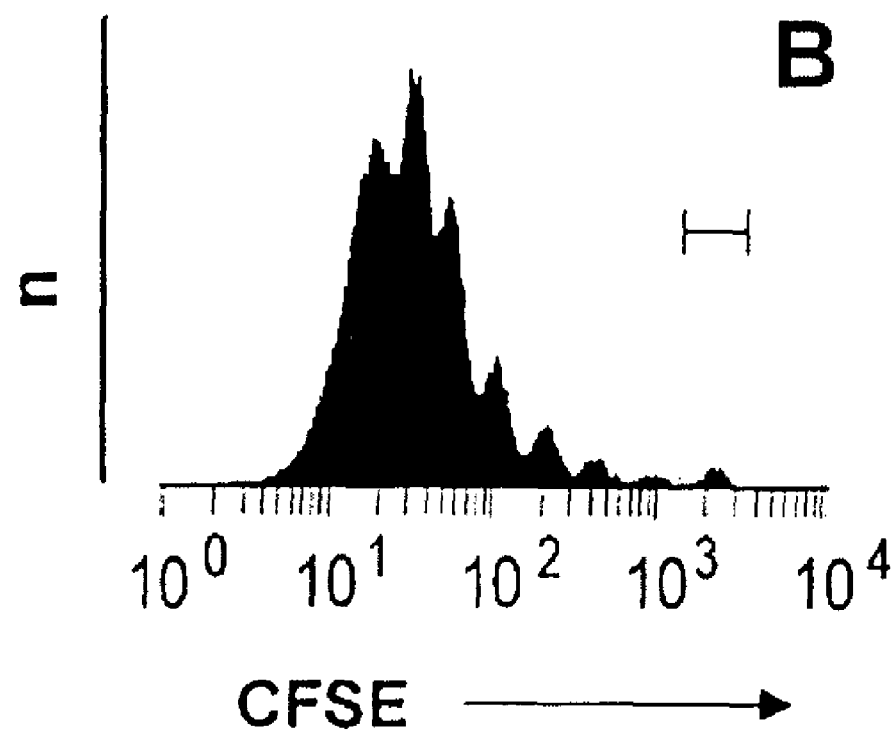

FIG. 14. Induction of proliferation in naïve CD4+ αβ T cells by TSST-1-loaded γδ T cells is cell contact-dependent.

Stimulated γδ T cells are loaded with 100 ng/ml TSST-1 and CFSE-labeled naïve CD4+ αβ T cells are cultured alone (A) or together (B) with γδ T cells at an APC:responder cell ratio of 1:5. The two-chamber culture system and the CFSE flow cytometry data analysis is described in FIG. 5.

Figure 15:
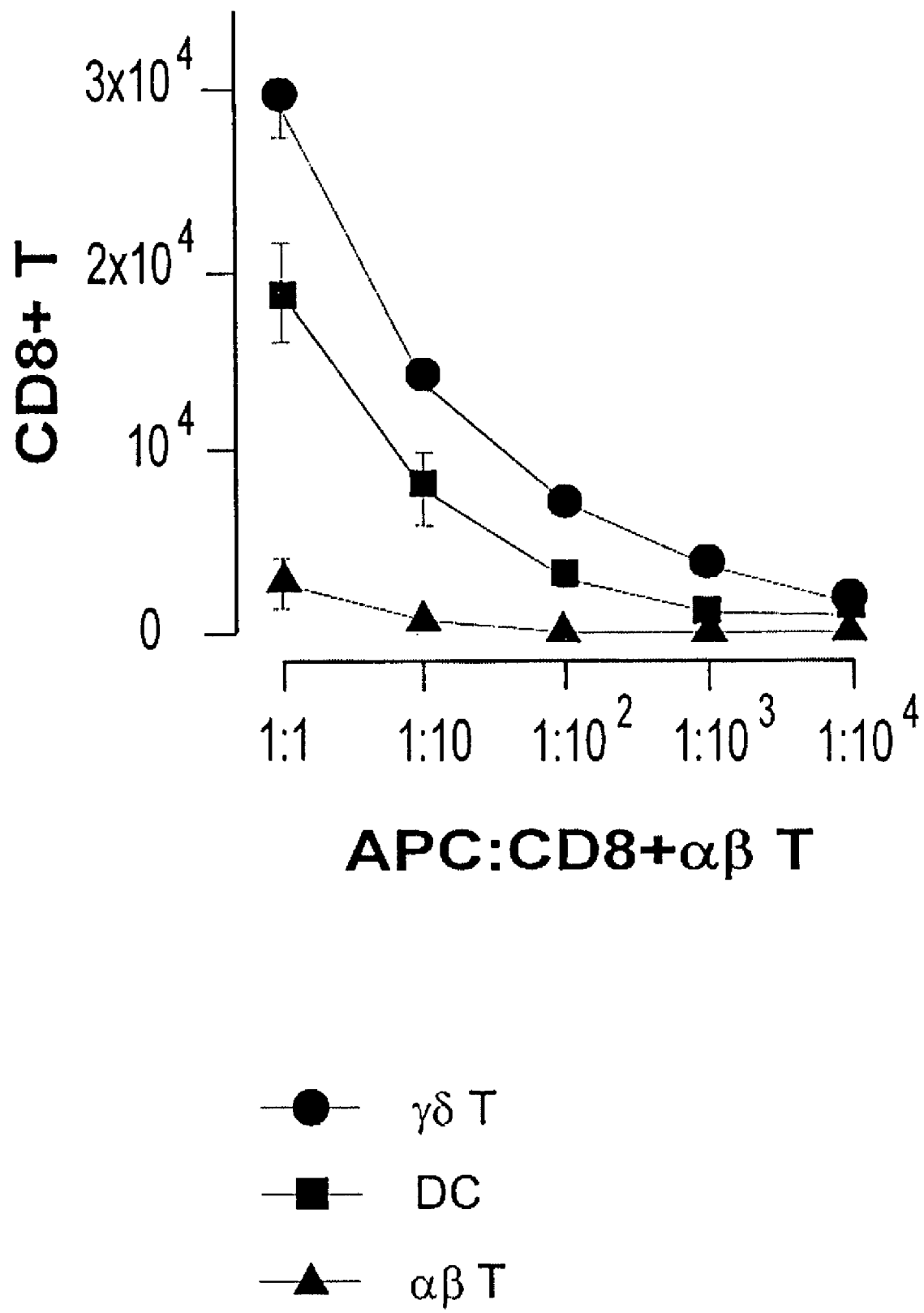

FIG. 15. γδ T cells induce primary CD8+ T cell responses.

Mixed-leukocyte responses with naïve, CD8+ αβ T cells and heterologous IPP-stimulated γδ T cells (circles), LPS-matured, monocyte-derived DCs (squares) or superantigen-stimulated αβ T cells (triangles) at decreasing APC:responder cell ratios (representative of 6 experiments). Proliferation responses in CFSE-labeled CD8+ responder cells were assessed by flow cytometry data analysis as described in FIG. 5.

Figure 16A:
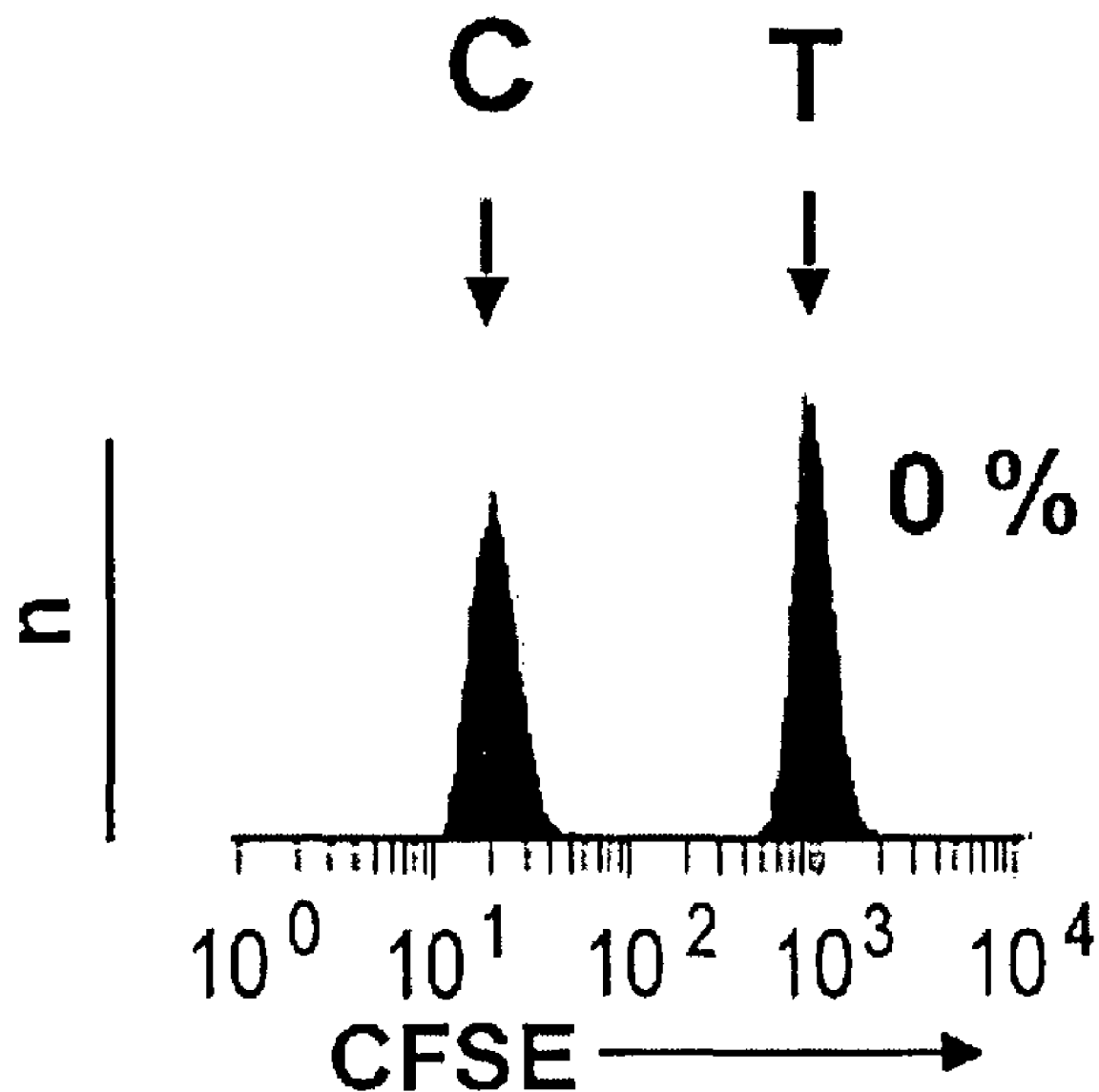
Figure 16B:
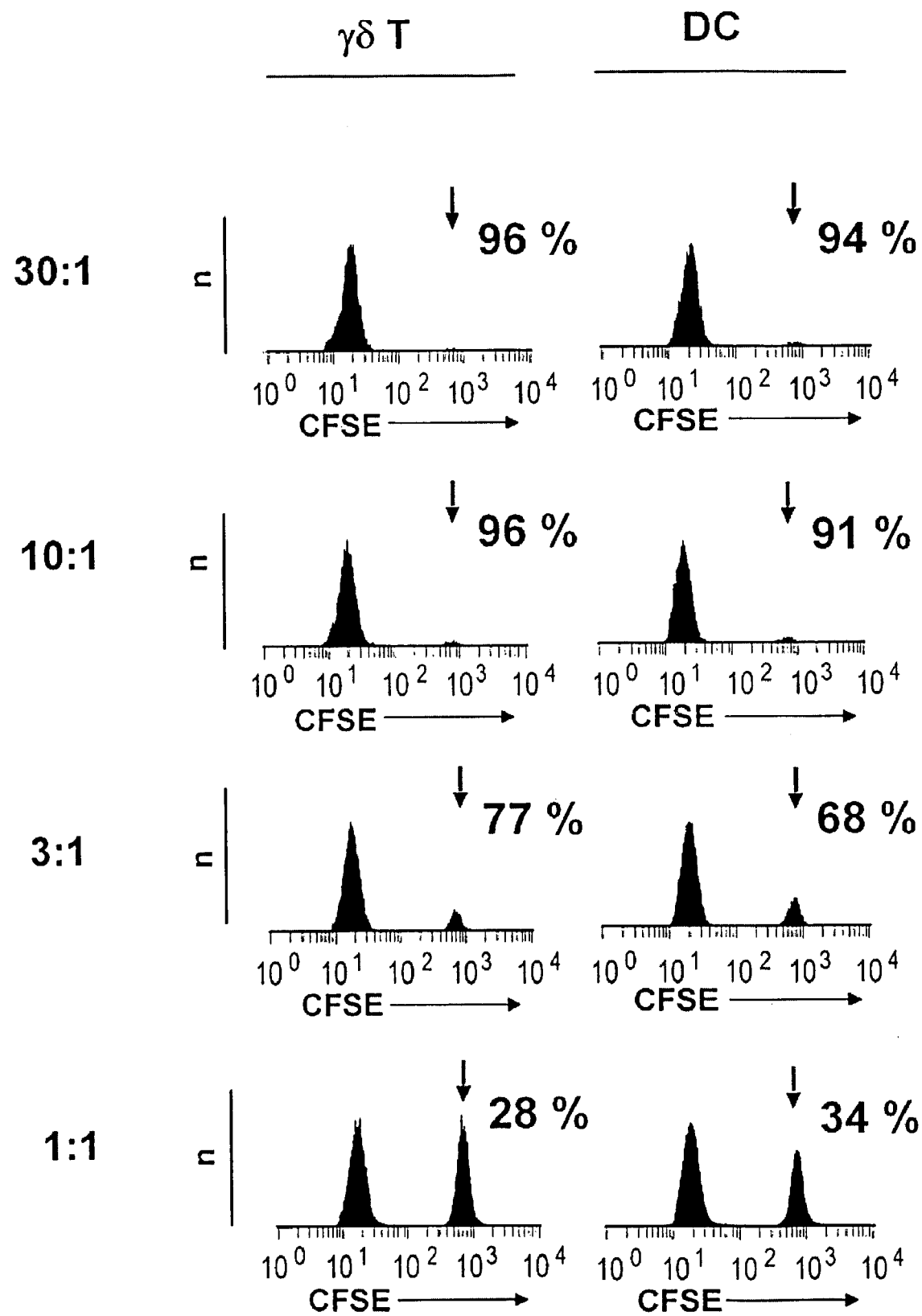

FIG. 16. γδ T cells induce differentiation of naïve CD8+ T cells into cytotoxic T cells.

CD8+ T cells derived from mixed-leukocyte responses, as described in FIG. 15, were examined after 14 days of culture for cytolytic activity. The cytotoxicity assay included effector cells, i.e. CD8+ T cells derived from mixed-leukocyte responses, and CFSE-labeled target cells. The mixture of target cells contained true target cells (heterologous CD4+ T cells) and negative control target cells (autologous CD4+ T cells) at a 1:1 ratio. True and negative control target cells were labeled with different concentrations of CFSE before mixing in order to discriminate between the two target cell subsets.

(A) Flow cytometric analysis of the target cell mixture in the absence of effector cells shows the negative control (C) and true target (T) cell populations.

(B) After 12 h of co-culture of CD8+ T cells and target cells at ratios of 30:1, 10:1, 3:1, and 1:1, the degree of target cell lysis was assessed by measuring the decrease in number in the true target cell population (arrow). The numbers by the arrows refer to percent specific killing and relate to loss of cell counts with high CFSE fluorescence (true target cells) as compared to control cell counts with low CFSE fluorescence.

Left column: CD8+ T cells were derived from mixed-leukocyte responses with IPP-stimulated γδ T cells as APCs.

Right column: CD8+ T cells were derived from mixed-leukocyte responses with mature DCs as APCs.

Figure 17:
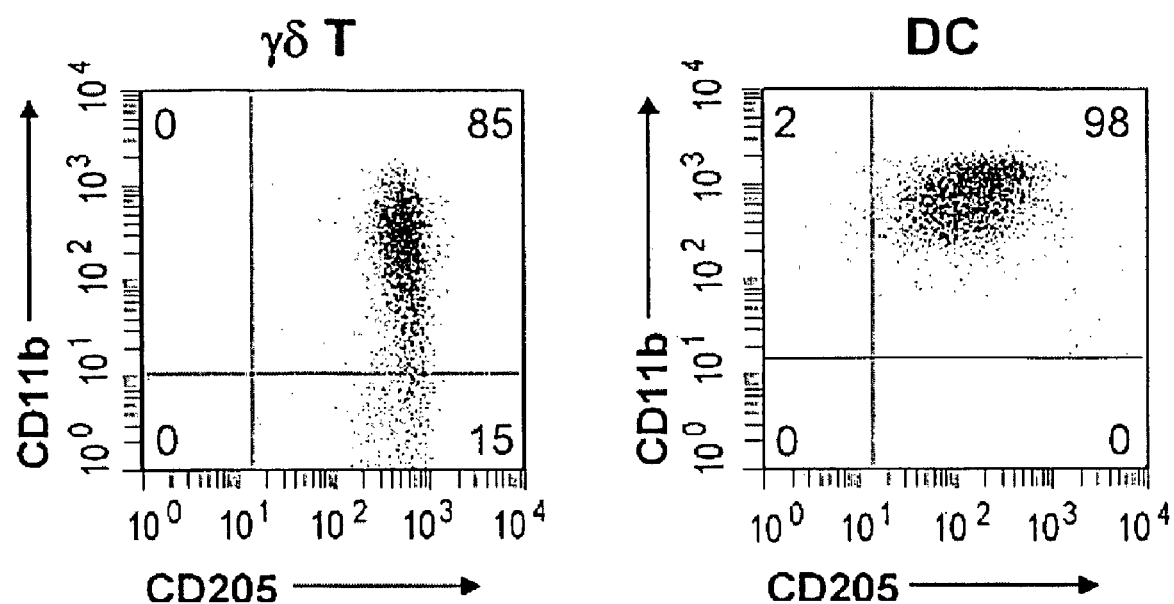

FIG. 17. γδ T cells express high levels of the endocytic cell surface proteins DEC205 (CD205) and CD11b.

γδ T cells freshly isolated from peripheral blood (γδ T) and immature DCs (DC) were analyzed for CD205 and CD11b expression by flow cytometry as described in FIG. 7. Vertical and horizontal lines in the dot-blots figure define the gates for CD205 or CD11b-expressing cells, and the right-upper quadrants in the figure depict cells double-positive for CD205 and CD11b; the numbers refer to the percent of total cells present within the individual quadrants. Positivity is defined by staining with isotype-matched control antibodies, and horizontal or vertical lines represent the gates for 99% background stainings.

DETAILED DESCRIPTION OF THE INVENTION

The flow diagram of the Scheme summarizes the method of invention for the preparation of efficient antigen-presenting human γδ T cells (Vγ2Vδ2+ γδ T cells, hereafter referred to as "γδ T cells") by isolation and in vitro treatment of human peripheral blood γδ T cells. Although protocols for isolation and in vitro proliferation of γδ T cells are known as such, the particular combination of stimulation and antigen application or peptide loading has not been described. Starting material is human peripheral blood that is processed by differential centrifugation or immunoabsorption to yield expanded or freshly isolated γδ T cells, respectively, at high purity. Short-term (e.g. 24 hours) stimulation in combination with antigen application or peptide loading results in γδ T cells with efficient antigen-presenting function for use in immunotherapy.

a) γδ T cells are readily expanded during culture of peripheral blood lymphocytes (PBLs) in the presence of isopentenyl pyrophosphate (IPP) or other small molecular weight non-peptide compounds with selectivity for γδ T cells as listed hereinbelow (Morita et al., 2000; Eberl et al., 2003). IPP or other small molecular weight non-peptide compounds with selectivity for γδ T cells are also used to induce antigen-presenting functions in selected γδ T cells as described hereinbelow. After 10-21 days in culture the vast majority of live, expanded cells are (Vγ2Vδ2+) γδ T cells, which are separated from dead cells by Ficoll-Paque centrifugation and used immediately for antigen-presenting cell (APC) generation or stored in liquid nitrogen. Alternatively, as described in "Examples", γδ T cells are directly isolated from peripheral blood mononuclear cells (PBMCs) by means of positive selection.

Scheme: Preparation of efficient antigen-presenting human γδ T cells

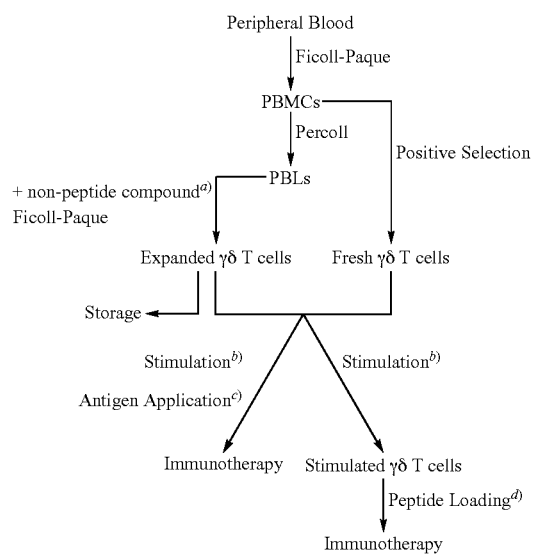

b) Isolated fresh or expanded γδ T cells are stimulated for a short period (e.g. 12 to 96 hours) with (Vγ2Vδ2+) γδ T cell-selective compounds or phytohemagglutinin (PHA) or other stimuli as listed hereinbelow for induction of antigen-uptake, of presentation function and of expression of co-stimulatory molecules.

c) γδ T cells are treated before, during or after stimulation (b) with antigens resulting in antigen-presenting γδ T cells. This antigen application includes a variety of independent approaches, such as (among others) addition of complex extracts or defined proteins from tumors, microbes or viral-infected cells or DNA/RNA encoding such pathogen-derived proteins, either in the form of purified nucleic material or packaged in expression vectors or attenuated viruses for transfection/transduction of γδ T cells and endogenous expression and processing of microbe-, pathogen- or tumor cell-derived antigens.

d) Instead of adding antigen (in the form of protein or DNA/RNA) to the γδ T cells during the short-term stimulation procedure (combinations of b and c), these steps may be performed sequentially. Stimulated γδ T cells are then "loaded" for a short period of time with defined peptide antigens that do not require intracellular proteolytic processing.

In addition to IPP, alternative small molecular weight non-peptide antigens with selectivity for (Vγ2Vδ2+) γδ T cells considered in step (a) are (E)-4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates. IPP is preferably applied as presented by B cells or substitutes.

Positive selection is, for example, performed by adding antibodies to human Vγ2Vδ2-TCRs to human peripheral blood mononuclear cells, e.g. 1-3 hours incubation, followed by magnetic cell sorting. Alternatively, positive selection may be performed by adding antibodies to human VγVδ-TCRs to human peripheral blood mononuclear cells (pan-γδ T cell selection) followed by magnetic cell sorting. (Vγ2Vδ2+) γδ T cell-selective compounds useful as stimuli for induction of antigen-presenting functions in Step (b) are IPP and other non-peptide compounds as listed above for step (a), e.g. 4-hydroxy-3-methyl-but-2-enyl pyrophosphate or other related microbial metabolites. Alternatively, PHA or other substitutes are useful as stimuli for induction of antigen-uptake, of presentation function and of expression of co-stimulatory molecules.

Stimulated cells may, if desirable, be irradiated in order to inhibit γδ T cell proliferation.

Examples of antigens applied as proteins in step (c) and/or (d) are those currently used in immunotherapy protocols employing DCs as antigen-presenting cells and are related to the therapeutic targets, e.g. tumor cells, infectious agents (microbes including viruses, bacteria, yeasts, and parasites), and pathogen-associated toxins. Such antigens include (but are not limited to) tumor-associated antigens (tumor-specific metabolic, structural and cell surface proteins, and the like); virus-associated antigens (virus-encoded envelope, structural, metabolic and enzymatic proteins, e.g. HIV gp120 proteins of different viral clades, HIV Tat, HIV proteases, e.g. envelope, structural, metabolic and enzymatic proteins derived from hepatitis viruses, influenza viruses, human cytomegalovirus, polio viruses, rabies viruses, herpes viruses, among others); bacteria-associated antigens (bacteria-encoded cell wall, structural, metabolic and enzymatic proteins, and the like, e.g. those derived from *Mycobacteria* (e.g. *M. tuberculosis, M. leprae*), *Listeria monocytogenes, Pneumococci, Staphylococci* (e.g. *S. aureus*), *Streptococci* (e.g. *S. pyogenes, S. pneumoniae*), *Vibrio cholerae, Clostridium tetani*, among others); yeast and fungi-associated antigens (yeast/fungi-encoded cell wall, structural, metabolic and enzymatic proteins, and the like, e.g. those derived from Candida albicans, Aspergillus fumigatus, among others); and pathogen-derived toxins (bacteria enterotoxins, e.g. staphylococcal enterotoxins, toxic shock syndrome toxin, tetanus toxins, among others). Examples of antigens applied as proteins also include those related to bacteria causing increased resistance to antibiotic treatment and those microorganisms causing life-threatening diseases world-wide (e.g. Plasmodia (for example P. falciparum, P. vivax, P. malariae), Leishmania, Trypanosoma, Entamoeba, Schistosoma, Filaria, among others). Antigens applied in step (c) in the form of RNA/DNA include those currently used in blood and tissue cell transfection protocols and include (but are not limited to) those encoding proteins from tumor cells, infectious agents (microbes including viruses, bacteria, yeasts, and parasites), and pathogen-associated toxins, as listed above.

"Efficient" as used in "efficient antigen-presenting human γδ T cells" means that the antigen-presenting functions of such cells are comparable to the corresponding antigen-presenting functions of DCs. "Efficient" is e.g. at least 10% as effective as with DCs under comparable conditions, the difference being a result of different cell morphology, including cell shape and surface area.

Short-term stimulated γδ T cells uniformly express the chemokine receptor CCR7, which is a prerequisite for homing of APCs to lymph nodes and Peyer's patches and, consequently, is a critical factor for initiation of adaptive immune responses. Resting peripheral blood γδ T cells do not express MHC-II molecules and, therefore, are not capable of presenting peptide antigens in a tolerogenic fashion. This issue of "safety" puts γδ T cells apart from other APCs, such as DCs and B cells, with known tolerance induction properties. Applications of antigen-presenting γδ T cells include, among others, the induction and/or improvement of immune responses against tumors in the treatment of tumor patients and against microbes and viruses in the treatment of patients with chronic infections or with inappropriate immune competence. In addition, antigen-presenting γδ T cells can be used for identification of novel tumor and otherwise pathogen-derived antigens with strong immunogenic properties for potential application in immunotherapy. Eventually, the application of γδ T cells to monitor the adaptive immune competence (status of immune competence) of immune-suppressed individuals (among others) is described.

The invention is now described in more detail with reference to the accompanying figures, which give ample proof of the efficiency of the method of the invention.

Figure 1A:
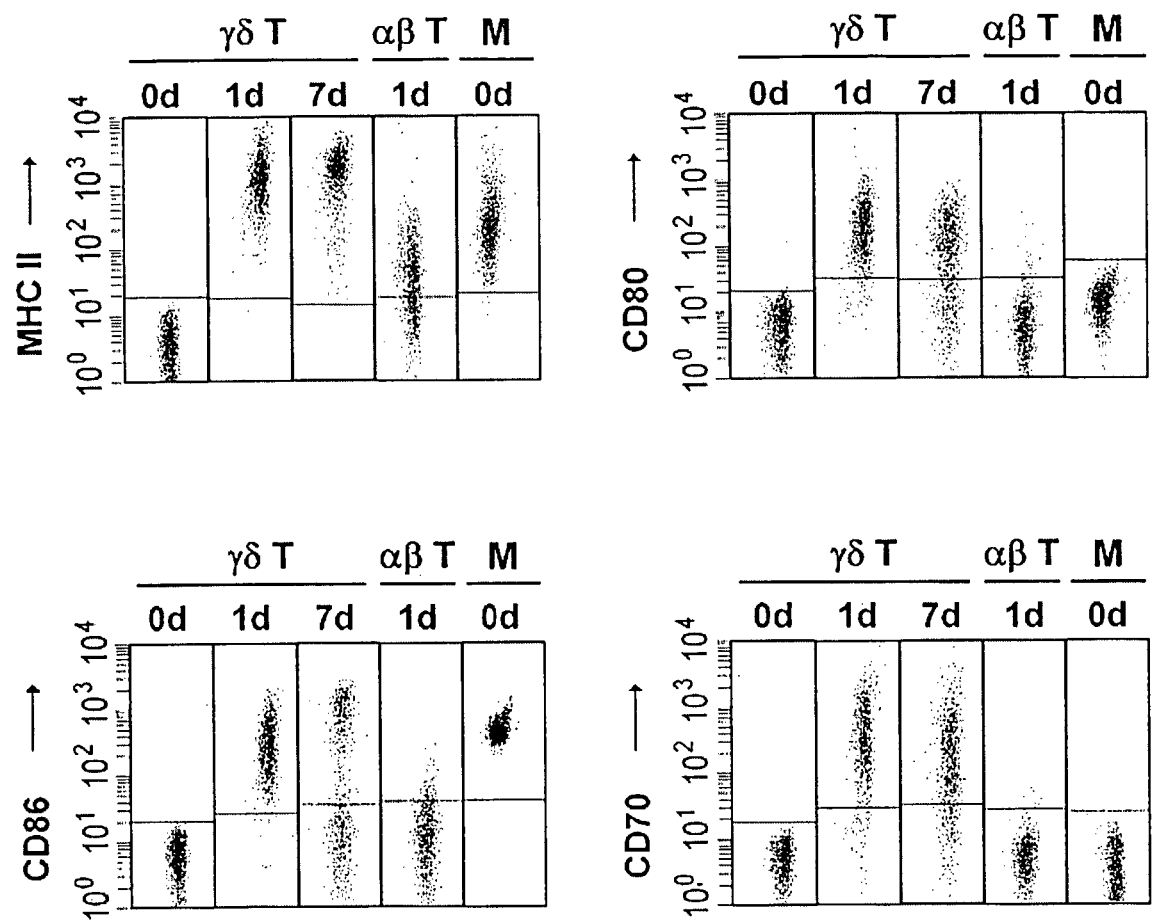
FIG. 1 (1A and 1B). Stimulated γδ T cells exhibit numerous antigen-presentation, co-stimulation and adhesion molecules.
Figure 1B:
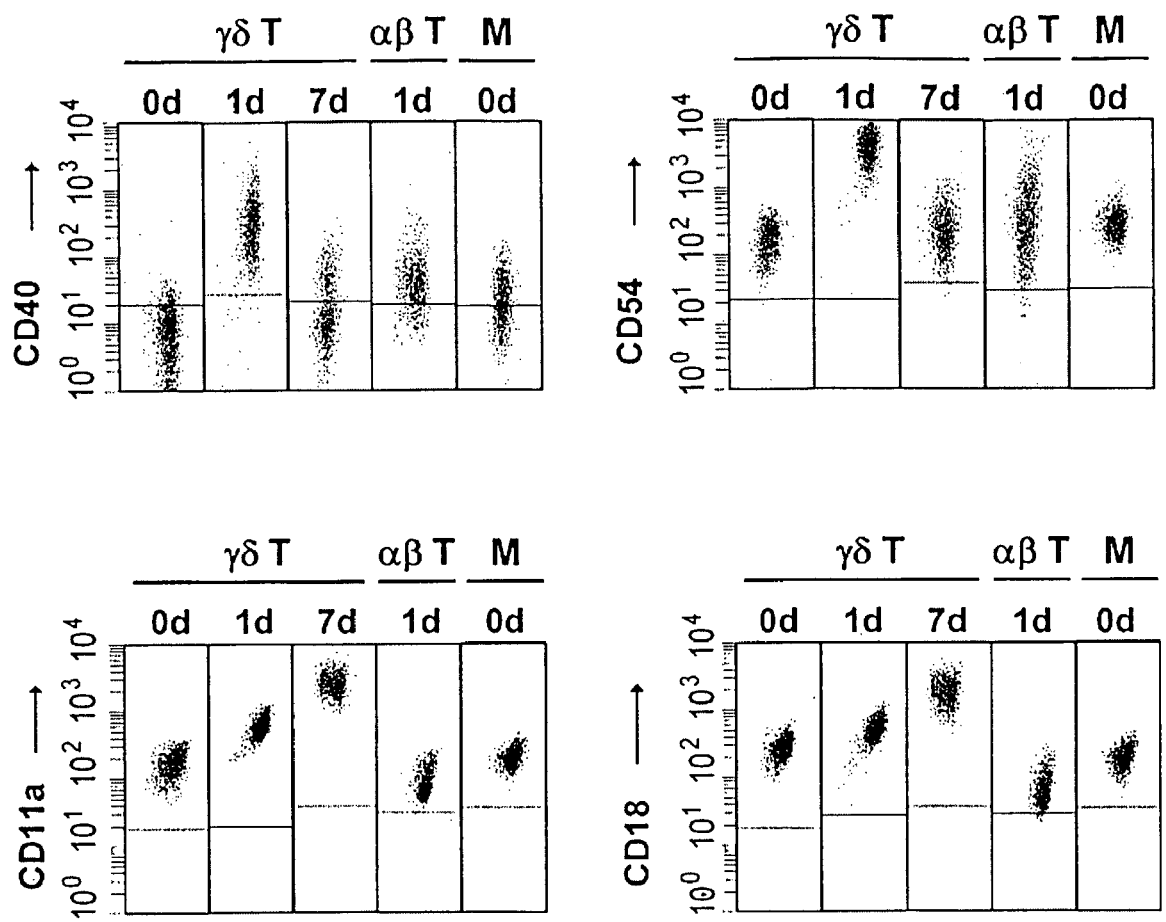

FIG. 1 describes the expression of cell surface molecules on γδ T cells, immediately after isolation from peripheral blood or after stimulation and culture for 1 or 7 days. For comparison, the same cell surface molecules are also examined on 1 day stimulated αβ T cells and freshly isolated monocytes. The cell surface molecules shown in FIG. 1 include MHC-II; the co-stimulatory molecules CD80 and CD86, the two selective ligands for the receptor CD28 present on naïve and memory T cells; CD70, the ligand for CD27; CD40, the receptor for CD154/CD40-ligand as well as the adhesion molecules CD54/ICAM-1, CD11a/αL-integrin, and CD18/β2-integrin, which are involved in cell-to-cell contact. These data demonstrate that freshly isolated γδ T cells have moderate levels of adhesion molecules but lack MHC-II and co-stimulatory molecules that are essential for the activation and differentiation of naïve T cells. By contrast, short-term (1 day) stimulation of γδ T cells results in very high levels of expression of MHC-II and co-stimulatory molecules and further enhance expression of adhesion molecules. Of note, and with the exception of CD40 and CD54, the levels of these cell surface molecules are maintained or further enhanced during culture of γδ T cells for 7 days. In clear contrast, the same series of molecules (with the exception of CD86 on monocytes) are moderately expressed or absent on αβ T cells and monocytes.

The numbers in Table 1 summarize the results from an extensive investigation of the expression of cell surface molecules on γδ T cells and, for comparison, on αβ T cells, monocytes and mature DCs. The list includes the examples shown in FIG. 1 as well as additional cell surface molecules. The numbers indicate the average expression levels, expressed as the mean of the mean fluorescence intensity (MFI), and the corresponding standard deviations (SD). Note the striking positivity of MHC-II (HLA-DR), co-stimulatory and adhesion molecules on activated γδ T cells that resembles mature DCs but exceeds by far the levels seen in activated αβ T cells and monocytes.

FIG. 2 and Table 2 correspond to previous results published by Brandes et al., 2003, and are included here to describe additional features of activated human γδ T cells that are pertinent to this invention. Table 2 lists the expression levels of chemokine receptors that differ clearly between freshly isolated peripheral blood γδ T cells and stimulated γδ T cells. γδ T cells in peripheral blood express chemokine receptors and adhesion molecules (shown in FIG. 1) for rapid recruitment to sites of inflammation and infection whereas short-term activation of γδ T cells partially inhibits these inflammatory migration properties (i.e. downmodulation of CCR2 and CCR5) and instead rapidly induces CCR7 expression for efficient homing to T cell areas of spleen, LNs and PPs.

TABLE 1

Expression levels of cell surface molecules on human γδ T cells.

|  | fresh γδ T cells MFI ± SD (n)[a] | 1 day γδ T cells MFI ± SD (n) | 7 days γδ T cells MFI ± SD (n) | 1 day γδ T cells MFI ± SD (n) | fresh monocytes MFI ± SD (n) | 8 h LPS DC MFI ± SD (n) |
|---|---|---|---|---|---|---|
| HLA-DR | 8 ± 13 (4) | 1738 ± 229 (4) | 2426 ± 1416 (4) | 368 ± 200 (8) | 743 ± 298 (4) | 1873 ± 142 (3) |
| CD80 | 0 ± 0 (3) | 157 ± 74 (3) | 115 ± 30 (4) | 3 ± 22 (8) | 2 ± 2 (6) | 109 ± 90 (3) |
| CD86 | 2 ± 1 (4) | 499 ± 249 (4) | 412 ± 256 (6) | 89 ± 89 (12) | 333 ± 130 (5) | 299 ± 325 (2) |
| CD70 | 0 ± 0 (4) | 293 ± 191 (5) | 422 ± 229 (3) | 11 ± 5 (6) | 0 ± 0 (4) | 0 ± 0 (2) |
| CD54 | 179 ± 44 (3) | 3589 ± 646 (3) | 511 ± 116 (3) | 949 ± 529 (6) | 602 ± 194 (3) | 1272 ± 605 (2) |
| CD11a | 274 ± 90 (3) | 651 ± 86 (2) | 2663 ± 919 (2) | 154 ± 8 (2) | 411 ± 179 (4) | 4 (1) |
| CD18 | 233 ± 60 (3) | 547 ± 18 (2) | 1174 ± 420 (2) | 129 ± 11 (2) | 283 ± 34 (4) | 5 (1) |
| CD40 | 10 ± 8 (3) | 684 ± 41 (2) | 46 ± 7 (3) | 108 ± 13 (4) | 69 ± 33 (3) | 493 ± 179 (2) |
| CD11b | 55 ± 11 (5) | 141 ± 63 (6) | 117 ± 182 (4) | 11 ± 6 (8) | n.d.[b] | 325 ± 118 (2) |
| CD11c | 8 ± 2 (2) | 100 ± 82 (3) | 168 ± 42 (2) | 46 (1) | n.d. | 453 ± 141 (2) |
| CD50 | 381 (1) | 347 ± 88 (2) | 347 ± 88 (2) | n.d. | n.d. | 30 ± 18 (2) |
| CD83 | 0 ± 0 (2) | 85 ± 79 (2) | 4 ± 1 (2) | n.d. | n.d. | 33 ± 22 (2) |

[a]Cells are stimulated and examined by flow cytometry for cell surface expression of indicated molecules as described in "Examples". MFI = mean fluorescence intensity; SD = standard deviation; (n) indicates the number of independent experiments.
[b]n.d. stands for not determined.

TABLE 2

Expression of chemokine receptors in human γδ T cells.

|  | Fresh γδ T cells % of positivity[a] mean ± S.D. (n) | Activated γδ T cells % of positivity mean ± S.D. (n) |
|---|---|---|
| CXCR3 | 66.5 ± 8.2 (10) | 65.9 ± 18.9 (9) |
| CXCR4 | 53.1 ± 13.8 (7) | 57.2 ± 21.6 (6) |
| CXCR5 | 2.3 ± 1.8 (7) | 2.0 ± 2.9 (5) |
| CCR1 | 20.6 ± 10.7 (5) | 24.5 ± 16.9 (4) |
| CCR2 | 23.0 ± 7.2 (9) | 14.1 ± 5.3 (7) |
| CCR4 | 13.3 ± 10.2 (12) | 29.9 ± 10.8 (12) |
| CCR5 | 61.2 ± 10.4 (12) | 2.5 ± 5.4 (9) |
| CCR6 | 20.1 ± 11.1 (6) | 15.2 ± 14.7 (4) |
| CCR7 | 18.9 ± 9.7 (23) | 77.6 ± 14.7 (14) |

[a]The data are taken from Brandes et al., Blood (2003)

FIG. 2 illustrates the migration properties of short-term activated γδ T cells, as assessed by in vitro chemotaxis analysis (Brandes et al., 2003). The data clearly demonstrate the responsiveness toward the CCR7 ligand SLC/CCL21 and the strongly reduced responsiveness toward the CCR5 (and CCR1, CCR3) ligand RANTES/CCL5 in activated γδ T cells. The data further demonstrate that changes in the level of cell surface chemokine receptors are directly mirrored in migration responses to the corresponding chemokines.

Collectively, the results summarized in FIGS. 1-2 and Tables 1-2 underscore the fact that stimulated but not resting (freshly isolated) γδ T cells from peripheral blood express many essential factors, including adhesion and co-stimulatory molecules, and chemokine receptors, required for LN-homing and stimulation of naïve T cells. The activation-induced modulation of these migration- and APC-related parameters compares well with the activation-induced changes occurring in DCs (Banchereau and Steinman, 1998; Steinman et al., 2003; Banchereau et al., 2004). Furthermore, these data imply that stimulated human γδ T cells act as potent APCs comparable to DCs.

Rapid, extensive and antigen-independent cell cluster formation is characteristic for DC-T cell interactions and is a prerequisite for antigen-dependent stimulation and differentiation of naïve T cells. FIG. 3 documents that stimulated γδ T cells also induce tremendous cell clustering with naïve (resting) CD4+ T cells within 3 hours of culturing. Of note, these clusters form in the absence of antigen, suggesting that adhesion and co-stimulatory molecules are responsible for this effect. The γδ T cell-mediated cluster formation is at least as robust as the one observed with mature DCs. By contrast, 1 day activated αβ T cells or freshly isolated monocytes (not shown) are much less efficient, which agrees with the reduced levels of adhesion and co-stimulatory molecules on these cells. These data provide further evidence that short-term activated γδ T cells have potent APC function.

Activated γδ T cells are able to take up, process and present antigen for triggering responses in antigen-specific CD4+ αβ T cell lines. FIG. 4 shows proliferation of tetanus toxoid (TT)-specific CD4+ αβ T cells in response to short-term stimulated, TT-presenting γδ T cells or, as control, TT-presenting DCs. The TT-specific CD4+ αβ T cell line is derived from the same donor who provided the γδ T cells. Resting TT-specific CD4+ αβ T cells are loaded with CFSE and proliferation of responder cells is determined by measuring the reduction of the CFSE signals in cultured cells by means of flow cytometry (see "Examples"). During cell division the CFSE content is distributed onto the two daughter cells such that each round of cell division is characterized by 50% reduction in CFSE signals. This type of analysis allows the determination of a) the fractions of non-responding versus proliferating cells (input/maximal versus reduced CFSE signals), b) the cellular subsets with distinct rounds of cell division, and c) the fraction of cells at the beginning of the experiment that has responded to the APCs. This information cannot be obtained by performing the $^3$H-thymidin-incorporation assay, which is an alternative method for the determination of cell proliferation. FIG. 4 shows that γδ T cells are capable of inducing proliferation in TT-specific CD4+ T cells and that this response fully depends on the antigen, since γδ T cells that have been stimulated in the absence of TT are inactive. It further shows that between day 4 and day 6 of culture the CD4+ T cells continue to proliferate, as evidenced by the further reduction of CFSE signals (shift to the left of fluorescence signals in FIG. 4). Of note, γδ T cells are similarly potent as mature DCs in this response, which demonstrates that short-term stimulated γδ T cells have potent antigen-presenting functions.

FIG. 5 illustrates the fact that the TT-specific proliferation responses require cell contact between TT-presenting γδ T cells and responding TT-specific CD4+ αβ T cells (responder cells). The responder cells that are separated by a porous membrane from co-cultures containing TT-presenting γδ T cells and responder cells do not proliferate. The porous membranes prevent the exchange of cells but do not prevent the exchange of soluble mediators between the two culture compartments. Therefore, the results in FIG. 5 also demonstrate that cytokines and growth factors produced during the co-culture of TT-presenting γδ T cells and responder cells have no effect on the proliferation of responder cells that are cultured separately.

TCR triggering is accompanied by TCR internalization, resulting in the downmodulation of cell surface TCR and accessory molecules, such as CD3. FIG. 6 documents that TT-presenting γδ T cells induce TCR downmodulation in TT-specific responder cells (see FIG. 4), as assessed by loss of cell surface CD3. Consequently, γδT cells have the capacity to take up and process TT and to present TT-derived peptides in the form of MHC-II-peptide complexes to TT-specific responder cells in a manner sufficient for TCR engagement. Since activated but not resting peripheral blood γδ T cells express cell surface MHC-II molecules, the antigen-presentation function is closely associated with γδ T cell activation. FIG. 6 also shows that TCR downmodulation is a function of the density of TT-peptides on stimulated γδ T cells, which is controlled by varying the amount of TT added during γδ T cell stimulation. Obviously, the more TT-derived MHC-II-peptide complexes are present on stimulated γδ T cells the more TCRs on responder cells become engaged and downmodulated. The different potency in TCR downmodulation between γδ T cells and DCs is likely due to striking differences in cell morphology, since the cell surface area in mature, antigen-presenting DCs is >10-fold larger than in stimulated γδ T cells (Miller et al., 2004).

In addition to proliferation, TT-presenting γδ T cells induce the expression of activation markers in TT-specific CD4+ αβ T cells. FIG. 7 shows the upregulation on the cell surface of responder cells of T cell activations markers, including CD25, ICOS and CD134/OX40, which are de novo expressed or enhanced in response to TCR triggering. As in induction of T cell proliferation, high-level expression of these activation markers fully depend on TT-peptide presentation by short-term stimulated γδ T cells, since these activation markers are not induced with γδ T cells, which are stimulated in the absence of TT.

FIG. 8 shows that heterologous Epstein Barr Virus (EBV)-immortalized B cells and autologous responder cells lack TT-presenting function. One protocol for stimulation of γδ T cells includes the use of irradiated, IPP-presenting cells that are either autologous B cells or, for convenience of in vitro experimentation, EBV-B cell lines, i.e. the heterologous CP.EBV line. FIG. 8 demonstrates that TT-treated CP.EBV cells fail to induce the proliferation of TT-specific CD4+ αβ T cells, indicating that CP.EBV material did not contribute to the strong proliferative responses obtained with TT-peptide presenting γδ T cells. Also, FIG. 8 illustrates the poor TT-presenting function of the αβ T cell line on its own.

Similar effects as those shown in FIGS. 4-8 with TT are obtained with the complex/undefined antigen Mycobacterium tuberculosis purified protein derivative (PPD). FIG. 9 shows the proliferation responses of PPD-specific CD4+ αβ T cells after 4 days or 8 days of culture following stimulation with PPD-peptide presenting γδ T cells or, alternatively, PPD-peptide presenting DCs as APCs. Again, the experiments are performed under autologous conditions, i.e. the APCs, (γδ T cells and DCs) and responder cells (PPD-specific CD4+ αβ T cell line) are derived from the same donor. As documented for TT, the proliferation responses are PPD-specific and do not differ substantially between γδ T cells and DCs. Also, the αβ T cell line itself fails to induce proliferation in PPD-specific responder cells. At equal concentrations of antigen γδ T cells and DCs induce more vigorous responses with TT as compared to PPD, which is due to the differences in the complexity between TT ($M_r$ [TT]: 150 kDa) and PPD ($M_r$ [PPD]: ≧10'000 kDa). Complex antigens, such as PPD or whole microorganisms, are highly diverse in the repertoire of antigenic peptides with the consequence that individual APCs present discrete MHC-peptide complexes at low levels. In agreement, TCR downmodulation is much less evident in cloned, PPD-specific CD4+ T cells during co-culture with PPD-presenting APCs than what is observed in the TT-system (FIG. 6).

Collectively, the experiments with TT-specific and PPD-specific responder cells document the finding of the present invention that stimulated (but not resting) γδ T cells derived from human peripheral blood have potent antigen uptake, antigen presentation and T cell stimulation functions. The potency and efficacy of these γδ T cells functions are remarkable and equal those obtained with DCs.

The characteristic of efficient APCs, such as DCs, is their ability to induce primary adaptive immune responses that involve the stimulation of naïve (antigen-inexperienced) T cells and their differentiation into antigen-specific effector T cells with the capacity to produce cytokines or to kill target cells (Banchereau and Steinman, 1998; Steinman et al., 2003; Banchereau et al., 2004). Fully differentiated memory T cells have reduced thresholds of activation, and TCR triggering in the absence of co-stimulation is sufficient to initiate effector functions. The experimental results shown in the following figures prove that stimulated γδ T cells also have efficient antigen-presenting functions comparable to those of DCs. Therefore, instead of antigen-experienced CD4+ αβ T cell lines (FIG. 4-9), autologous freshly isolated naïve CD4+ αβ T cells are used as potential responder cells.

FIG. 10 shows the extent of proliferation in CFSE-labeled, naïve CD4+ αβ T cells in response to toxic shock syndrome toxin (TSST-1 )-loaded, short-term stimulated γδ T cells and TSST-1-loaded mature DCs, as opposed to TSST-1-loaded stimulated γδ T cells or TSST-1-loaded freshly isolated monocytes. TSST-1 binds to MHC-II molecules on APCs and is selective for αβ-TCRs containing the Vβ2-chain. 4-10% of peripheral blood CD3+ T cells are Vβ2+ and respond with high affinity to TSST-1-presenting APCs. As demonstrated in FIG. 10, TSST-1-loaded γδ T cells are expert APCs in induction of proliferation in naïve Vβ2+-T cells, as evidenced by the reduction of CFSE signals, and this response is much more prominent in naïve CD4+ αβ T cells bearing Vβ2+-TCRs than those bearing Vβ2$^{neg}$-TCRs. Eventually, after completion of cell expansion most of the resulting memory T cells express Vβ2+-TCRs (see also Table 3). Importantly, the proliferation responses equal the ones obtained with TSST-1-loaded DCs. Under these conditions, TSST-1-loaded ac T cells or monocytes are completely inactive, indicating that the level of TSST-1-presentation and/or co-stimulation in these cells is not sufficient to induce efficient primary T cell responses.

TABLE 3

αβ T cell expansion and Th cell differentiation during long-term culture (21 days)

| APCs[a] | Ratio | Antigen[b] | ng/ml | Vβ2+ (%)[c] | Th0 (%)[d] | Th1 (%) | Th2 (%) |
|---|---|---|---|---|---|---|---|
| γδ T | 1:5 | TSST-1 | 10 | 32 | 18 | 25 | 16 |
| γδ T | 1:1 | TSST-1 | 10 | 70 | 2 | 73 | 1 |
| γδ T | 1:5 | TSST-1 | 100 | 99 | 9 | 46 | 6 |
| γδ T | 1:5 | TSST-1 | 1000 | 93 | 13 | 50 | 5 |
| DC | 1:5 | TSST-1 | 10 | 80 | 6 | 84 | <1 |
| DC | 1:5 | TSST-1 | 100 | 83 | 2 | 86 | <1 |
| DC | 1:5 | TSST-1 | 1000 | 67 | 1 | 82 | <1 |
| — | | PHA | 1000 | 9 | n.d.[e] | n.d. | n.d. |

[a]APCs are either 1 day stimulated γδ T cells or mature DCs that are loaded with TSST-1 and added to naïve CD4+ αβ T cells at the ratio of 1:5 or 1:1.
[b]TSST-1 is the antigen used to load the APCs; alternatively, naïve CD4+ αβ T cells are directly activated with PHA in the absence of APCs.
[c]The percent Vβ2+ responder cells is determined by flow cytometry as described in FIG. 10.
[d]The fraction in percent of cytokine polarized Th cells is determined by measuring intracellular cytokines as described in FIG. 13.
[e]Data not determined.

In addition to co-stimulatory molecules, the parameters that largely determine the kinetics and extent of proliferation in naïve CD4+ αβ T cells are the density of MHC-II-TSST-1 complexes on APCs and the ratio between APCs and responder cells. FIG. 11 shows the proliferation of Vβ2+ naïve responder cells in response to increasing concentrations of TSST-1 that are used to load the different types of APCs. Before addition to naïve CD4+ αβ T cells, the APCs are washed to get rid off excess TSST-1 (see "Examples"). The list of autologous APCs includes 1 day stimulated or 7 day stimulated γδ T cells, mature DCs, freshly isolated monocytes and 1 day stimulated αβ T cells. 1 day stimulated γδ T cells induce T cell proliferation responses at TSST-1 loading concentrations as low as 1 ng/ml and are equally efficient as DCs in terms of maximal responses. The approx. 10-fold higher potency of DCs may be due to their greatly enlarged cell surface area (Miller et al., 2004), which allows more frequent or extensive contacts with responder cells (see also FIG. 6). Of note, substantial proliferation responses are still obtained with stimulated γδ T cells that are expanded during culture for 7 days before loading with TSST-1. Obviously, γδ T cells maintain APC functions over extended periods of time, which is in agreement with the observed conservation of adhesion and co-stimulatory molecules (see also FIG. 1 and Table 1). Monocytes and αβ T cells are >100-fold less potent than γδ T cells. These data demonstrate that stimulated γδ T cells have efficient antigen-presenting functions.

In the experiment shown in FIG. 12, instead of titration of TSST-1 during APC loading, the ratio of APCs to naïve responder cells is varied between 1:5 to 1:200 while keeping the TSST-1 loading concentration at 100 ng/ml or 1 μg/ml. Proliferation responses of naïve Vβ2+ CD4+ αβ T cells are determined as in FIG. 11. There is no obvious difference between 1 day stimulated γδ T cells and DCs, and at highest APC dilution (1:200) the proliferation responses still range between 28-40% of maximal responses. These data further illustrate the proficiency of γδ T cells as efficient APCs.

Primary immune responses involve the differentiation of naïve CD4+ T cells into polarized Th1, Th2 or Th0 cells with the capacity to produce type 1 (IFN-γ), type 2 (IL-4) or type 0 (IFN-γ+IL-4) cytokines, respectively. Naïve CD4+ T cells have the capacity to differentiate into either one of these polarized Th cells. T cell polarization is determined by the co-stimulatory environment provided by APCs at the time of naïve T cell priming. Efficient APCs not only induce proliferation of naïve T cells but also support their differentiation into effector cells. FIG. 13 demonstrates that stimulated γδ T cells are fully capable of presenting TSST-1 in the proper context of co-stimulation for the generation of effector Th cells. 4 days after priming with TSST-1-loaded γδ T cells, most Vβ2⁺ naïve CD4⁺ T cells have responded by proliferation and expression of the memory marker CD45RO. After 21 days of culture the majority of cells return to a resting state, uniformly express CD45RO and consist of Vβ2⁺ T cells (Table 3). Importantly, the majority of cells produce cytokines typical of either Th1, Th2 or Th0 cells, and Th1 polarization is further enhanced by increasing the ratio of TSST-1-loaded γδ T cells and responder cells to 1:1. Again, the more prominent effect seen with DCs may be due to morphological criterion as discussed above (Miller et al., 2004) (see also FIGS. 6, 9). By contrast, antigen-unselective activation (phytohemagglutinin) does not result in selective expansion of Vβ2⁺ T cells (Table 3), and stimulated ad T cells fail to induce CD45RO expression and proliferation of naïve CD4⁺ αβ T cells (FIG. 13).

As seen with TT-specific and PPD-specific CD4⁺ αβ T cells (see e.g. FIG. 5), induction of responses in naïve CD4⁺ as T cells is fully dependent on cell-to-cell contact with TSST-1-loaded γδ T cells (FIG. 14). Stimulated γδ T cells induce strong antigen-specific responses in naïve CD4⁺ as T cells and support their proliferation and differentiation in a manner typical for efficient APCs.

CD4⁺ T cells recognize MHC class II-peptide complexes on APCs whereas CD8⁺ T cells recognize MHC class I-peptide complexes on APCs. MHC class I molecules are ubiquitously expressed on blood and tissue cells; therefore, all cells in the body are potential target cells for CD8⁺ T cells. Of note, CD8⁺ T cells are crucial players in the defense against viral infections and tumors and, frequently, successful vaccination depends on the generation of antigen-selective, cytotoxic CD8⁺ T cells. FIG. 15 documents that Vβ2⁺ T cells are highly potent APCs in the induction of primary CD8⁺ T cell responses. Naïve, untouched CD8⁺ as T cells are used as responder cells in proliferation assays containing IPP-stimulated γδ T cells, mature DCs or superantigen-stimulated αβ T cells as APCs (all from the same donor). γδ T cells fully match or are even better as DCs in induction of CD8⁺ T cell proliferation, and asp T cells are inferior APCs. FIG. 16 documents that γδ T cells induce the differentiation of cytotoxic effector T cells. The data illustrate that γδ T cells are indistinguishable from DCs in driving the differentiation of naïve CD8⁺ T cells into alloantigen-specific, cytotoxic T cells. Collectively, TCR-stimulated Vδ2⁺ T cells induce strong proinflammatory responses in both naïve CD4⁺ and CD8⁺ αβ T cells in a "professional" APC-like manner.

γδ T cells also express endocytic receptors, such as the C-type lectin DEC-205 (CD205) and the integrin subunit CD11b with selectivity for multiple protein and non-protein ligands. CD205 and CD11b are known to be highly expressed on DCs (Banchereau and Steinman, 1998; Steinman et al., 2003; Banchereau et al., 2004). FIG. 17 documents that γδ T cells, similar to DCs, inherently express high levels of these endocytic receptors. In analogy to novel methods of antigen-delivery to DCs, these data demonstrate that antigens, including protein vaccines for tumors and infectious agents, can also be targeted to γδ T cells for in vivo antigen processing and presentation.

These experimental details prove that the method of the invention for the preparation of efficient antigen-presenting human γδ T cells comprising selecting γδ T cells out of human peripheral blood mononuclear cells, treating the selected cells with a stimulus for induction of antigen-presenting functions, and applying the antigen to the stimulated cells provides ACPs comparable to DCs.

In particular, the invention concerns such a method for the preparation of efficient antigen-presenting human γδ T cells wherein selecting γδ T cells is performed by magnetic cell sorting with antibodies to human VγVδ-T cell receptors. Alternatively, selecting γδ T cells is performed by culturing freshly isolated peripheral blood lymphocytes in the presence of structurally defined small molecular weight non-peptide compounds that induce the selective expansion of Vγ2Vδ2⁺-T cell receptor chain-expressing γδ T cells, for example in the presence of IPP, e.g. as presented by B cells or substitutes.

The invention further concerns the particular method wherein the stimulus for induction of efficient antigen-presenting functions is a small molecular weight non-peptide compound or a substitute or phytohemagglutinin, and the particular method wherein the antigen is applied in the form of defined proteins, undefined protein mixtures, or crude or enriched extracts from tumor and infected cells, for example wherein the antigen applied is a pathogen- or tumor cell-derived peptide, or a pathogen-derived protein which is applied in the form of DNA or RNA encoding it under conditions allowing endogenous expression of said pathogen-derived protein, in particular in the form of purified DNA or RNA or a delivery vector containing such DNA or RNA. If the antigen is in the form of a DNA or RNA conditions are selected such that said DNA or RNA may be properly expressed. Application of an antigen may occur before, during or after γδ T cell stimulation for induction of antigen-presenting functions. If an antigen is applied as a peptide (protein fragment), its application may also be after stimulation in a separate step termed "peptide loading".

The efficient antigen-presenting human γδ T cells prepared according to the invention as described hereinbefore may be used in immunotherapy. Such use may be similar to the known use of DCs in immunotherapy, thereby overcoming the drawbacks of the use of DCs such as scarcity in peripheral blood, inability to proliferate in vitro, heterogeneity and functional instability.

In particular, the efficient antigen-presenting human γδ T cells prepared according to the invention as described hereinbefore may be used for the manufacture of a medicament (pharmaceutical composition) for use in immunotherapy.

The present invention relates also to pharmaceutical compositions that comprise the efficient antigen-presenting human γδ T cells prepared according to the invention as described hereinbefore, and that can be used especially in the treatment of the diseases mentioned hereinbefore and hereinafter. Compositions for parenteral administration, such as intravenous, intramuscular, subcutaneous, mucosal or submucosal administration, to humans are especially preferred. The compositions comprise the cells together with a pharmaceutically acceptable carrier. The dosage of the cells of the invention depends upon the disease to be treated and upon the age, weight, and individual condition, the individual pharmacokinetic data, and the mode of administration. The pharmaceutical compositions comprise from approximately 0.01% to approximately 50% of the cells of the invention. Unit dose forms are, for example, ampoules or vials.

Preference is given to the use of isotonic aqueous suspensions. The pharmaceutical compositions may comprise excipients, for example preservatives, stabilizers, wetting agents and/or emulsifiers, solubilizers, salts for regulating osmotic pressure and/or buffers and are prepared in a manner known per se, for example by means of conventional mixing processes. The manufacture of injectable preparations is usually carried out under sterile conditions, as is the filling, for example, into ampoules or vials, and the sealing of the containers.

The invention further relates to a method of treatment of tumors or chronic or recurrent infectious diseases wherein efficient antigen-presenting human γδ T cells are injected into a patient in need thereof. In particular the method involves single or repeated applications of said γδ T cells, e.g. pharmaceutical compositions containing same, by intradermal, subcutaneous, intramuscular, intravenous, mucosal or submucosal routes.

In the method of treatment of tumors γδ T cells are used, which have been stimulated in the presence of defined tumor proteins or crude (undefined) tumor cell extracts or, alternatively, which have been obtained using treatment with recombinant RNA/DNA technologies that are routinely used for transfection or transduction of live blood or tissue cells. Preferably, if defined tumor peptides for direct loading onto cell surface MHC molecules are known, then such peptides are added to stimulated γδ T cells, incubated, washed and immediately used for therapy. It is important to emphasize that the number of γδ T cells used per administration as well as the route and frequency of γδ T cell administration depend on the efficacy in immune response induction by the individual tumor antigen used as well as the type and location of the tumor present in the individual patient. Preferred protocols are, for example, $1-20 \times 10^6$ cells/0.5-2 ml per administration with 1 to 6 follow-up administrations with the same or lower amounts of cells at two-weeks to two-months intervals.

In the method of treatment of chronic or recurrent infectious diseases γδ T cells are used which have been stimulated in the presence of defined infectious agents, preferably in attenuated form, or crude (undefined) infected cell extracts or, alternatively, which have been obtained using treatment with recombinant RNA/DNA technologies that are routinely used for transfection or transduction of live blood or tissue cells. The preferred treatment protocol corresponds to the one described above.

The invention further relates to a method of vaccination against tumors or chronic or recurrent infectious diseases wherein efficient antigen-presenting human γδ T cells, to which non-infectious and non-tumorigenic antigens have been applied, are injected into a patient to be vaccinated. For vaccination purposes the same procedures are applied as described hereinbefore but wherein γδ T cells are used to which non-infectious and non-tumorigenic antigens have been applied. The preparation of vaccine antigen-presenting γδ T cells and administration of these cells for the vaccination of patients against tumor antigens or infectious agents follows the description of tumor immunotherapy (see above). Preferred protocols are those currently employed in DC-based vaccination treatments. The immune status of such treated patients, i.e. the quality (efficacy, kinetics, etc.) of the vaccine responses, is examined as described below.

The invention further relates to another method of (prophylactic or therapeutic) vaccination against tumors or vaccination against agents inducing infectious or non-infectious diseases, comprising the administration of γδ T cell-targeting vaccines to individuals. Preferably, such γδ T cell-targeting vaccines are hybrid compounds composed of vaccine agents and γδ T cell-targeting molecules. γδ T cell-targeting molecules are antibodies or ligands specific for endocytic receptors on γδ T cells, including but not limited to CD11b and CD205. Vaccine agents are proteins or related molecules against which an immune protection is desired.

Administration of γδ T cell-targeting vaccines entails the repeated treatment of individuals with γδ T cell-targeting vaccines by means of injections, oral administrations or any other protocol of vaccine delivery yielding optimal immune protection.

The invention further relates to a method of identification of novel tumor or pathogen-derived antigens comprising selecting γδ T cells out of human peripheral blood mononuclear cells, treating the selected cells with a stimulus for induction of efficient antigen-presenting functions, applying fractions of an undefined protein mixture, or crude or enriched extracts from tumor and infected cells, or RNA or DNA libraries derived from tumors and infectious agents, testing for in vitro activation of autologous naïve αβ T cells, and comparing the activation results of different antigen fractions.

In this method, γδ T cells are used as in vitro screening tools for the identification of novel and improved antigens for use in therapeutic and prophylactic vaccinations. Isolating, selecting and stimulating γδ T cells are performed as described in the method of preparation of efficient antigen-presenting human γδ T cells. In the step of applying antigens, fractions of crude antigen preparations (e.g. cell extracts or undefined mixtures) or RNA/DNA libraries derived from tumors and infectious agents are used. Such prepared γδ T cells are then tested for activation of naïve up T cells from the same donor, i.e. autologous αβ T cells. Read-outs in these in vitro immune response assays are proliferation and cytokine production in αβ T cells, or any other simple measurement of αβ T cell activation. Culture conditions are preferably those described above for αβ T cell responses to TSST-1-presenting γδ T cells in FIGS. 10-14 and the "Examples". When comparing activation results from different antigen fractions, improved αβ T cell responses indicate that the antigen sources are "enriched" in terms of immunogenicity. Corresponding "enriched" fractions are further processed, and the whole cycle of experimental steps repeated with the further fractionated antigens. Eventually, repeated fractionation of "enriched" antigen sources (protein or DNA library fractionation) leads to single proteins with maximal immunostimulatory functions. Such novel proteins may be further manipulated by proteolytic cleavage, and cleavage mixtures analyzed accordingly for the generation of (small) immunogenic peptides for direct loading onto APCs.

The invention further relates to a method of diagnosing the immune competence of a patient comprising selecting γδ T cells out of the patient's peripheral blood mononuclear cells, treating the selected cells with a stimulus for induction of efficient antigen-presenting functions, applying the antigen for which the immune competence has to be determined, and testing for in vitro activation of autologous αβ T cells.

In this method, γδ T cells and their impact on antigen-specific memory αβ T cells from the same donor are used as in vitro tools for the diagnosis of the immune competence of a patient with regard to a particular antigen and for determination whether a vaccination has been successful. Isolating, selecting and stimulating γδ T cells are performed as described in the method of preparation of efficient antigen-presenting human γδ T cells. In the step of applying antigens, the particular antigen for which immune competence has to be determined, is applied to stimulated γδ T cells. Culture conditions and read-outs for determination of αβ T cell responses (in vitro immune response assays) are preferably those described above for αβ T cell responses to TSST-1-presenting γδ T cells in FIGS. 10-14 and the "Examples". The decisive difference is that memory αβ T cells instead of naïve αβ T cells are monitored for enhanced immune responses (proliferation, cytokine production, etc.) during stimulation with antigen-presenting γδ T cells. Successful immunotherapy (vaccination) leads to the generation of antigen-specific effector/memory T cells, which will give many fold improved immune responses during in vitro monitoring of immune status as compared to naïve αβ T cells. These assays are preferentially performed with bulk (unfractionated) αβ T cells, since antigen-specific memory αβ T cells are highly enriched in successfully vaccinated individuals.

EXAMPLES

Abbreviations
DC dendritic cell
LN lymph node
PP Peyer's patch
TCR T cell antigen receptor
BCR B cell antigen receptor
MHC major histocompatibility complex
APC antigen-presenting cell
Vδ1+ T cells Vδ1+-TCR chain expressing γδ T cells
Vγ2Vδ2+ T cells Vγ2Vδ2+-TCR chain expressing γδ T cells
IPP isopentenyl pyrophosphate
TT *Clostridium tetani* tetanus toxin
PPD *Mycobacterium tuberculosis* purified protein derivative
TSST-1 *Staphylococcus aureus* toxic shock syndrome toxin 1
PHA phytohemagglutinin
IFN-γ interferon-γ
TNF-α tumor necrosis factor-α
IL interleukin
FACS fluorescence-activated cell sorter
MFI mean fluorescence intensity
SD standard error
CFSE carboxyfluorescein diacetate succinimidyl ester 1. Cell Isolation and Generation γδ T Cells Human peripheral blood mononuclear cells (PBMCs) are isolated from heparin-treated donor blood buffy coats or fresh blood by Ficoll-Paque centrifugation according to standard protocols (Brandes et al., 2003). Out of PBMCs, γδ T cells are positively selected with antibodies to human VγVδ-TCRs using the magnetic cell sorting system from Miltenyi Biotec. In this way, 50 ml of fresh blood routinely yields 2–5×10$^6$ cells with a purity of 98-99% γδ T cells.

Naïve αβ T Cells

Untouched, naïve CD4+ or CD8+ αβ T cells (98-99% purity) are isolated from PBMCs by negative magnetic cell sorting with specific antibodies to VγVδ-TCR, CD1c, CD14, CD16, CD19, CD25, CD45RO, CD56, HLA-DR plus CD4 or CD8, respectively, followed by fluorescence-activated cell sorting of cells that stain negative for these markers.

αβ T Cell Lines

From PBMCs CD4+ αβ T cells are positively selected with antibodies to human CD4 by means of the magnetic cell sorting. CD4+ a T cells are stimulated with TT- or PPD-presenting autologous, irradiated (30 Gy) PBMCs at a ratio 1:100 in the first and 1:10 in the following cycles, and are expanded in IL-2 containing medium. Antigen-specificity is verified by a CFSE-based proliferation assay (see below) after three cycles of antigenic selection and expansion.

B Cells

B cells are isolated by negative magnetic cell sorting out of PBMCs. B cells are either used directly for γδ T cell stimulation (see below), or B cell lines are generated by EBV-induced transformation following standard protocols and then used for γδ T cells stimulation.

Monocytes

Monocytes are isolated by positive magnetic cell sorting from PBMCs with antibodies to human CD14, and stringent washing of the separation columns before elution of magnetically trapped cells results in enrichment of CD14$^{high}$ monocytes.

DCs

Monocyte-derived DCs are generated by culturing CD14$^{high}$ cells in medium containing 10% FCS in the presence of IL-4 (10 ng/ml) and GM-CSF (25 ng/ml). After 6-7 days of culture the majority of cells is immature, as assessed by cell surface staining for HLA-DR, CD1a, CD14, CD80, CD83, CD86 and CCR7. DC maturation is induced by further culture for 8 hours in the presence of 100 ng/ml LPS (from *Salmonella abortus equi*) (Langenkamp et al., 2000). DC maturation is confirmed by flow cytometry staining for cell surface DC maturation markers HLA-DR, CD80, CD83, CD86 and CCR7.

2. T Cell Stimulation

γδ T Cells

50 µM isopentenyl pyrophosphate (IPP) presented by heterologous or autologous EBV-transformed B cell lines or primary B cells at a dilution of 1:10 is used to activate resting (freshly isolated) γδ T cells as described (Brandes et al., 2003). γδ T cells are cultured in medium supplemented with 8% human serum in the presence of IL-2 (20 or 200 IU/ml).

αβ T Cells

Positive selected αβ T cells are activated on plates coated with 10 µg/ml anti-CD3 antibody (OCT3) plus 250 ng/ml anti-CD28 antibody (28.2) or, alternatively, with 10 ng/ml phorbol 12-myristate 13-acetate (PMA) plus 1 µg/ml ionomycin or, alternatively, with 1 µg/ml PHA, and cultured in medium supplemented with 8% human serum in the presence of IL-2 (200 IU/ml).

3. Carboxyfluorescein Diacetate Succinimidyl Ester (CFSE) Labeling

Cells are washed with PBS and labeled with 2.5 µM CFSE (Molecular Probes, Eugene, OR) in PBS⁻ supplemented with 1% FCS for 4 min at room temperature. Labeling is stopped by repeated washing of the cells with ice-cold PBS⁻ supplemented with 5% FCS. The CFSE-labeled cells are immediately used in cell activation and proliferation assays.

4. In vitro Antigen-Presentation Assays

Antigen Presentation to αβ T Cell Lines

Blood γδ T cells are activated by the IPP-presenting and irradiated (100 Gy) heterologous EBV-B cell line CP-EBV (see above) for 24 to 60 hours in the presence of 10-20 µg/ml TT (Berna Biotech, Bern, Switzerland) or 20 µg/ml PPD (Statens Serum Institut Copenhagen, Denmark). Monocyte-derived DCs are cultured with TT or PPD for the same period of time and matured for the last 8 hours (see above). After irradiation (26 and 40 Gy for γδ T cells and DCs, respectively) and intensive washing, these APCs are used to stimulate TT- and PPD-specific CD4+ αβ T cells clones at a ratio of 1:5 (if not indicated otherwise). At various time points of culture responder cells are examined by flow cytometry for expression of activation markers (HLA-DR, ICOS, and CD25), TCR internalization (loss of cell surface CD3) and cell proliferation (reduction in CFSE fluorescence signals).

Priming of Naïve CD4+ αβ T Cells

Following stimulation of γδ T cells and αβ T cells or following maturation of monocyte-derived DCs or following isolation of monocytes from PBMCs, these potential APCs are pulsed for 1 hour at 37° C. with various concentrations of toxic shock syndrome toxin (TSST-1) (Toxin Technology, Sarasota, Fla.). Then, the potential APCs are irradiated with 12 Gy (or 40 Gy for DCs), extensively washed and mixed (routinely at a ratio 1:5) with CFSE-labeled naïve CD4+ αβ T cells. Generally, 96-well round bottom plates contain 8×10$^3$ APCs and 4×10$^4$ CFSE-labeled responder cells in culture medium without exogenous cytokines. Cell proliferation is analyzed after 4 days by flow cytometry. In Th cell differentiation assays, 100 IU/ml IL-2 is added on day 5 of culture, and cells are expanded during subsequent 10-16 days until responder cells cease to proliferate and return to a resting state (Langenkamp et al., 2000). At day 21, Th cell differentiation is examined by measuring intracellular cytokine production. Cells are stimulated for 6 hours with PMA/ionomycin in the presence of 10 µg/ml Brefeldin A (Sigma-Aldrich), then fixed with 2% paraformaldehyde, permeabilized with 0.5% saponin in PBS containing 2% FCS, stained with antibodies to IL-2, IFN-γ, IL-4 and Vβ2-TCR, and analyzed by flow cytometry.

Priming of Naïve CDLR αβ T Cells

In mixed-leukocyte responses, irradiated, IPP-stimulated γδ T cells, superantigen-activated αβ T cells or LPS-maturated DCs are co-cultured with heterologous CFSE-labeled naïve CD8$^+$ αβ T cells. Generally, 96-well round bottom plates contain $4\times10^4$ CFSE-labeled responder cells and APCs in the range of $4\times10^4$ cells to 4 cells per well, corresponding to APC:responder cell ratios of 1:1 to 1:10'000. Cell proliferation is analyzed after 6 days of culture by flow cytometry. CD8$^+$ effector cell generation is evaluated, after 14 days of mixed-leukocyte responses with naïve CD8$^+$ αβ T cells, in a cytolytic assay, involving co-culture for 12 h with a mixture of heterologous (true targets) and autologous (negative control) CD4$^+$ T cells labeled with high (1 µM) and low dose (0.05 µM) of CFSE, respectively, followed by flow cytometry analyzing CFSE signals. Reduction in the counts of true target cells indicates antigen-specific killing by CD8$^+$ effector cells whereas reduction in the counts of negative control cells indicates unspecific target cell killing by CD8$^+$ effector cells.

5. Culture Media

The medium used throughout is RPMI 1640 supplemented with 2 mM L-glutamine, 1% nonessential amino acids, 1% sodium pyruvate, 50 µg/ml penicillin/streptomycin, $5\times10^{-5}$ M 2-mercaptoethanol and either 10% FCS (Hyclone Laboratories, Logan, Utah, or GIBCO BRL) or 8% human serum (Swiss Red Cross, Bern, Switzerland). Human recombinant IL-2 is produced using the myeloma-based expression system.

6. Flow Cytometry

Cell Preparation

Cells are washed twice in ice-cold PBS$^-$ supplemented with 2% FCS and 0.01% sodium-acid. After blocking for 10 min with 10 mg/ml human immunoglobulin, cells are sequentially incubated for 20 min on ice with primary antibodies specific for diverse cellular proteins or isotype-matched control antibodies, washed, and in case of untagged primary antibodies, further incubated with fluorescence tag-labeled secondary reagents. After final washing, cells-associated fluorescence is measured with a FACSCalibur (Becton Dickinson, San Jose, Calif.), and the recorded data re analyzed by the CellQuestPro software (Becton Dickinson).

Antibodies

Source of antibodies: Mouse mAbs anti-CD1a (HI149), CD3 (UCHT1), CD4 (RPA-T4), CD8 (HIT8α), CD11b (D12), CD14 (MΦP9), CD16 (3G8), CD19 (HIB19), CD20 (2H7), CD25 (M-A251), CD40 (5C3), CD45RA (HI100), CD45RO (UCHL-1), CD50 (TU41), CD54 (HA58), CD56 (B159), CDw70 (Ki-24), CD80 (L307.4), CD83 (HB15e), CD86 (2331; FUN1), CD134 (L106), CD205 (MG38), HLA-DR (G46-6), pan-VγVδ-TCR (11F2), IL-2 (MQ1-17H12), IL-4 (8D4-8), IFNγ (B27), and IL-10 (No 20705A) from BD PharMingen, San Diego, Calif.; mouse mAbs anti-CD1a (Nal/34-HLK) and CD19 (HD37) from DAKO Diagnostics, Glastrup, Sweden; mouse mAB anti-TCRVβ2 (MPB2D5) from Immunotech, Marseille, France; mouse mAB anti-CD138 (B-B4) from Diaclone, Besancon, France; mAB anti-CD102 (B-T1) from Leinco Technologies, St. Louis, Mo.; mouse mAbs anti-CD11a (TS1-22) and CD18 (TS1-18) from R. Pardi, Milano, Italy; mouse mAb anti-ICOS (F44) from R. A. Kroczek, Berlin, Germany; rat mAb anti-CCR7 (3D12) from M. Lipp, Berlin, Germany. These are used for flow cytometric analysis or cell isolation. The following secondary Ab, conjugates and control Ab are used: RPE-conjugated goat anti-mouse IgG from Sigma-Aldrich, St. Louis, Mo.; RPE-conjugated donkey anti-rat IgG from Jackson ImmunoResearch Laboratories, West Grove, Pa.; RPE as well as RPE-Cy5 conjugated streptavidine (SA) from DAKO; APC conjugated SA from BD PharMingen; mouse control IgG1 (MOPC21) from Sigma-Aldrich; other isotype-matching control Abs from BD PharMingen.

7. Immunotherapy of Tumors or Chronic/Recurrent Infections

For the preparation of stimulated, tumor antigen-presenting γδ T cells, 50-150 ml of peripheral blood is drawn from tumor patients (or patients with chronic/recurrent infections, see below) and γδ T cells isolation and antigen loading is performed as described above. Alternatively, such freshly isolated γδ T cells are expanded by in vitro culture under Vγ2Vδ2$^+$-TCR-stimulatory conditions (see methods of γδ T cell activation with IPP above) in the presence of 20-1000 IU/ml IL-2 and then stored in liquid nitrogen for later use in the preparation of tumor (or vaccine, see below) antigen-presenting γδ T cells. Importantly, instead of defined tumor/vaccine proteins, many other ways of antigen delivery to γδ T cells for the preparation of APCs are possible, including (among others) addition of crude (undefined) tumor cell extracts or extracts from infected cells (see below) or, alternatively, the treatment of γδ T cells by recombinant RNA/DNA technologies that are routinely used for transfection or transduction of live blood or tissue cells. Also, if defined tumor (or vaccine, see below) peptides for direct loading onto cell surface MHC molecules are known, then such peptides at 0.1-10 µg/ml are added to stimulated γδ T cells at $1\times10\times10^6$ cells/ml, which are then incubated at 20-37° C. for short period of time, washed 2-times with isotonic phosphate-buffered saline solution and immediately used for therapy. It is important to emphasize that the number of γδ T cells used per administration as well as the route and frequency of γδ T cells administration depend on the efficacy in immune response induction by the individual tumor (or vaccine, see below) antigen used as well as the type and location of the tumor present in the individual patient. Protocols follow those currently employed in DC-based immunotherapies (Fong and Engleman, 2000; Steinman et al., 2003; Schuler et al., 2003; Figdor et al., 2004), i.e. $1\times20\times10^6$ cells/0.5-2 ml per administration with 1 to 6 follow-up administrations with the same or lower amounts of cells at two-weeks to two-months intervals.

References

Banchereau, J., Pascual, V., and Palucka, A. K. (2004). Autoimmunity through cytokine-induced dendritic cell activation. Immunity. 20, 539-550.

Banchereau, J. and Steinman, R. M. (1998). Dendritic cells and the control of immunity. Nature 392, 245-252.

Brandes, M., Willimann, K., Lang, A. B., Nam, K. H., Jin, C., Brenner, M. B., Morita, C. T., and Moser, B. (2003). Flexible migration program regulates gamma delta T-cell involvement in humoral immunity. Blood 102, 3693-3701.

Carding, S. R. and Egan, P. J. (2002). Gammadelta T cells: functional plasticity and heterogeneity. Nat. Rev. Immunol. 2, 336-345.

Chen, Z. W. and Letvin, N. L. (2003). Adaptive immune response of Vgamma2Vdelta2 T cells: a new paradigm. Trends Immunol. 24, 213-219.

Eberl, M., Hintz, M., Reichenberg, A., Kollas, A. K., Wiesner, J., and Jomaa, H. (2003). Microbial isoprenoid biosynthesis and human gammadelta T cell activation. FEBS Lett. 544, 4-10.

Figdor, C. G., de Vries, I. J., Lesterhuis, W. J., and Melief, C. J. (2004). Dendritic cell immunotherapy: mapping the way. Nat. Med. 10, 475-480.

Fong, L. and Engleman, E. G. (2000). Dendritic cells in cancer immunotherapy. Annu. Rev. Immunol. 18, 245-273.

Langenkamp, A., Messi, M., Lanzavecchia, A., and Sallusto, F. (2000). Kinetics of dendritic cell activation: impact on priming of TH1, TH2 and nonpolarized T cells. Nat. Immunol. 1, 311-316.

Miller, M. J., Hejazi, A. S., Wei, S. H., Cahalan, M. D., and Parker, I. (2004). T cell repertoire scanning is promoted by dynamic dendritic cell behavior and random T cell motility in the lymph node. Proc. Natl. Acad. Sci. U. S. A 101, 998-1003.

Morita, C. T., Mariuzza, R. A., and Brenner, M. B. (2000). Antigen recognition by human gamma delta T cells: pattern recognition by the adaptive immune system. Springer Semin. Immunopathol. 22, 191-217.

Moser, B., Wolf, M., Walz, A., and Loetscher, P. (2004). Chemokines: multiple levels of leukocyte migration control. Trends Immunol. 25, 75-84.

Schuler, G., Schuler-Thurner, B., and Steinman, R. M. (2003). The use of dendritic cells in cancer immunotherapy. Curr. Opin. Immunol. 15, 138-147.

Steinman, R. M., Hawiger, D., and Nussenzweig, M. C. (2003). Tolerogenic dendritic cells. Annu. Rev. Immunol. 21, 685-711.

Zhong, G., Reis e Sousa, and Germain, R. N. (1997). Antigen-unspecific B cells and lymphoid dendritic cells both show extensive surface expression of processed antigen-major histocompatibility complex class II complexes after soluble protein exposure in vivo or in vitro. J. Exp. Med. 186, 673-682.

The invention claimed is:

1. A method for the preparation of efficient antigen-presenting human γδ T cells comprising:
    selecting γδ T cells out of human peripheral blood mononuclear cells, treating the selected cells with a stimulus for induction of antigen-presenting functions, and applying an antigen for uptake and presentation by these cells, the applied antigen being at least one pathogen-derived protein which is applied in the form of a purified DNA or RNA or a delivery vector containing such DNA or RNA and encoding it under conditions allowing endogenous expression of said pathogen-derived protein;
    wherein selecting γδ T cells is performed by culturing freshly isolated peripheral blood lymphocytes in the presence of structurally defined small molecular weight non-peptide compounds that induce the selective expansion of Vγ2Vδ2$^+$-T cell receptor chain-expressing γδ T cells;
    further wherein the structurally defined small molecular weight non-peptide compounds are selected from at least one of isopentenyl pyrophosphate, 4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

2. The method of claim 1 wherein the structurally defined small molecular weight non-peptide compound is isopentenyl pyrophosphate.

3. The method of claim 1 wherein the stimulus for induction of antigen-presenting functions is a structurally defined small molecular weight non-peptide compound selected from at least one of isopentenyl pyrophosphate, 4-hydroxy-3-methyl-but-2-enyl pyrophosphate (HMB-PP), ethyl pyrophosphate (EPP), farnesyl pyrophosphate (FPP), dimethylallyl phosphate (DMAP), dimethylallyl pyrophosphate (DMAPP), ethyl-adenosine triphosphate (EPPPA), geranyl pyrophosphate (GPP), geranylgeranyl pyrophosphate (GGPP), isopentenyl-adenosine triphosphate (IPPPA), monoethyl phosphate (MEP), monoethyl pyrophosphate (MEPP), 3-formyl-1-butyl-pyrophosphate (TUBAg 1), X-pyrophosphate (TUBAg 2), 3-formyl-1-butyl-uridine triphosphate (TUBAg 3), 3-formyl-1-butyl-deoxythymidine triphosphate (TUBAg 4), monoethyl alkylamines, allyl pyrophosphate, crotoyl pyrophosphate, dimethylallyl-γ-uridine triphosphate, crotoyl-γ-uridine triphosphate, allyl-γ-uridine triphosphate, ethylamine, isobutylamine, sec-butylamine, iso-amylamine and nitrogen containing bisphosphonates.

4. The method of claim 3 wherein the structurally defined small molecular weight non-peptide compound is isopentenyl pyrophosphate.

5. The method of claim 3 wherein the structurally defined small molecular weight non-peptide compound is 4-hydroxy-3-methyl-but-2-enyl pyrophosphate.

6. The method of claim 1 wherein the stimulus for induction of antigen-presenting functions is phytohemagglutinin.

* * * * *